(12) United States Patent
Meier

(10) Patent No.: US 12,305,151 B2
(45) Date of Patent: May 20, 2025

(54) PHOTOBIOREACTOR, IN PARTICULAR FOR THE PRODUCTION OF MICRO-ORGANISMS SUCH AS MICROALGAE

(71) Applicant: Anita Meier, Weichering (DE)

(72) Inventor: Anita Meier, Weichering (DE)

( * ) Notice: Subject to any disclaimer, the term of this patent is extended or adjusted under 35 U.S.C. 154(b) by 777 days.

(21) Appl. No.: 17/616,796

(22) PCT Filed: Jun. 3, 2020

(86) PCT No.: PCT/EP2020/065280
§ 371 (c)(1),
(2) Date: Dec. 6, 2021

(87) PCT Pub. No.: WO2020/245149
PCT Pub. Date: Dec. 10, 2020

(65) Prior Publication Data
US 2022/0315874 A1    Oct. 6, 2022

(30) Foreign Application Priority Data
Jun. 4, 2019    (DE) .................... 10 2019 114 979.7

(51) Int. Cl.
*C12M 1/00*    (2006.01)
*C12M 3/00*    (2006.01)

(52) U.S. Cl.
CPC ............ *C12M 21/02* (2013.01); *C12M 23/02* (2013.01); *C12M 23/34* (2013.01); *C12M 23/44* (2013.01); *C12M 31/10* (2013.01)

(58) Field of Classification Search
CPC ...... C12M 21/02; C12M 23/02; C12M 23/34; C12M 23/44; C12M 23/06; C12M 23/22; C12M 23/58; C12M 31/10; C12M 31/08
See application file for complete search history.

(56) References Cited

U.S. PATENT DOCUMENTS

| 3,837,494 A | 9/1974 | Stevenson |
| 5,080,793 A | 1/1992 | Urlings |

(Continued)

FOREIGN PATENT DOCUMENTS

| DE | 19611855 C1 * | 8/1997 | ............ B01J 19/127 |
| DE | 102013109747 A1 | 3/2015 | |

(Continued)

OTHER PUBLICATIONS

Machine Translation of DE19611855C1 (Year: 2024).*

*Primary Examiner* — Michael L Hobbs
(74) *Attorney, Agent, or Firm* — Laurence A. Greenberg; Werner H. Stemer; Ralph E. Locher

(57) ABSTRACT

A photobioreactor is particularly suited for producing micro-organisms such as microalgae. The photobioreactor is a closed reactor with reactor vessels which have an open top that is closed by a top wall of the photobioreactor and in which a nutrient medium can be held. At least some of the reactor vessels are individual vessels. Adjacent reactor vessels form a gap between a front wall and a rear wall, the gap being closed at the top side by an overflow wall region and having a vessel overflow opening between the adjacent reactor vessels. A lighting element is held in the gap. Each of the reactor vessels has a partition which divides the reactor vessel into a front reactor chamber and a rear reactor chamber. At least one partition through-flow opening between the front and rear reactor chambers is formed in the partition close to the bottom wall.

33 Claims, 7 Drawing Sheets

(56) References Cited

U.S. PATENT DOCUMENTS

| | | | | |
|---|---|---|---|---|
| 5,447,629 A | * | 9/1995 | Chaumont | ............ C12M 41/10 |
| | | | | 210/197 |
| 8,895,289 B2 | | 11/2014 | Mohr et al. | |
| 2010/0323436 A1 | | 12/2010 | Lee et al. | |

FOREIGN PATENT DOCUMENTS

| | | | | |
|---|---|---|---|---|
| DE | 102016215119 A1 | * | 2/2018 | ............ C12M 1/42 |
| EP | 0442157 A1 | | 8/1991 | |
| EP | 2326706 B1 | | 4/2012 | |
| EP | 3041924 B1 | | 4/2018 | |
| WO | 2005068605 A1 | | 7/2005 | |
| WO | 2009094680 A1 | | 8/2009 | |

* cited by examiner

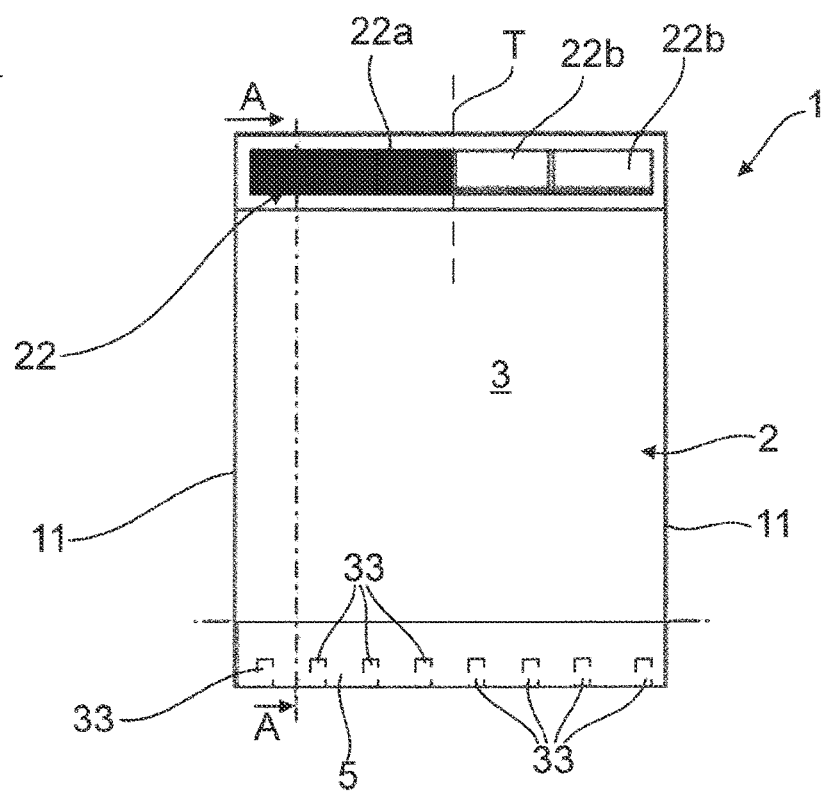
Fig. 1
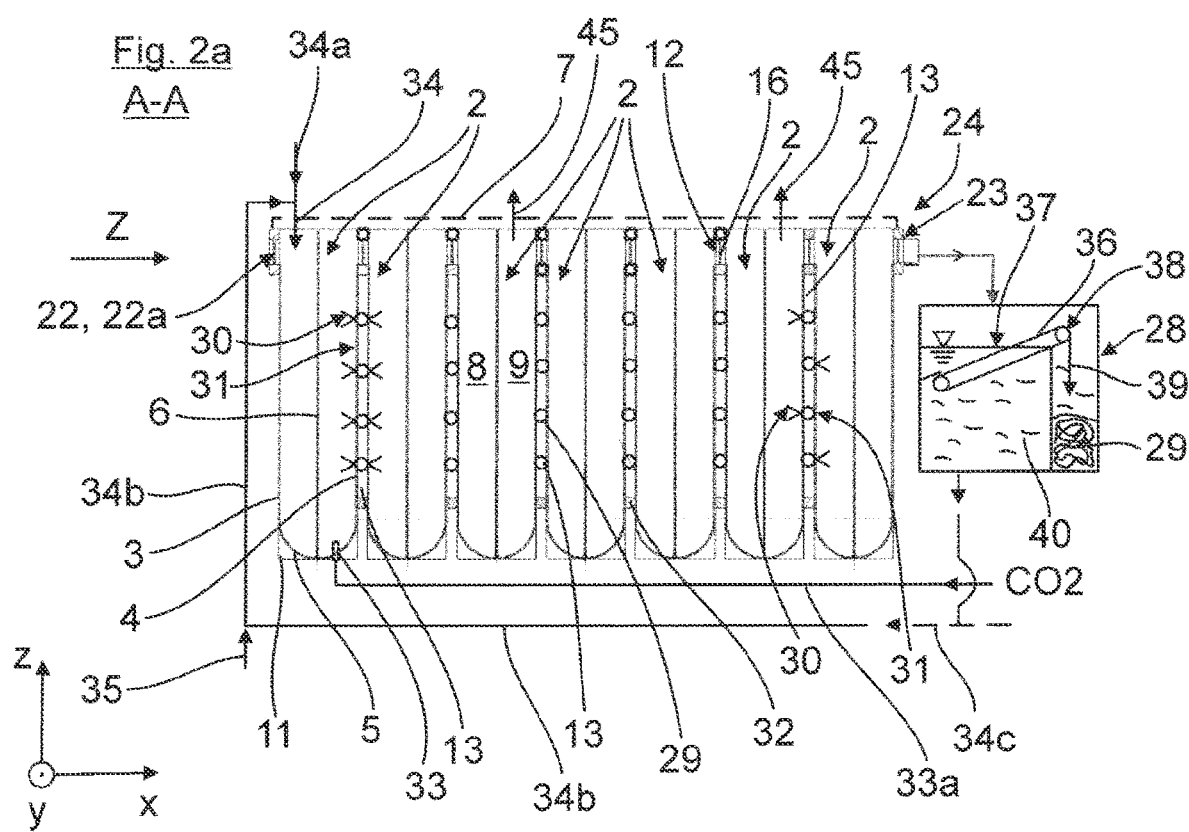
Fig. 2a A-A

PHOTOBIOREACTOR, IN PARTICULAR FOR THE PRODUCTION OF MICRO-ORGANISMS SUCH AS MICROALGAE

FIELD AND BACKGROUND OF THE INVENTION

The invention relates to a photobioreactor, especially for the production of microorganisms, wherein the photobioreactor is designed as a closed reactor comprising a plurality of upwardly open reactor vessels which are closed by a one-piece or multi-piece, preferably removable, top wall of the photobioreactor and in which a nutrient medium is accommodable, to a reactor vessel for a photobioreactor and to a method for producing microorganisms, especially microalgae.

Microalgae are prokaryotic and eukaryotic photosynthetic microorganisms distinguished by simple cellular material. Depending on the species, the size of microalgae can vary from a few micrometers up to a few hundred micrometers (µm). Microalgae can either live as single cells or form colonies. Depending on their size, microalgae can be divided into four main categories: microplankton (20-1000 µm), nanoplankton (2-100 µm), ultraplankton (0.5-15 µm) and picoplankton (0.2-2 µm). Important microalgae types for industrial production are, for example, Chlorella vulgaris, Spirulina (Arthrospira) and Nannochloropsis, to name just a few examples.

Owing to their morphological and physiological properties, microalgae are used in various biotechnological processes, such as, for example, in the production of antioxidants, drugs, immunostimulants, biofuels, peptides, polymers, toxins, sterols and food supplements, to name just a few examples. Depending on the type of microalgae used, the biomass cultivation and the subsequent processing, valuable molecules and compounds such as fat, oil, polyunsaturated fatty acids, natural dyes, various polysaccharides, pigments, bioactive molecules, etc., can also be obtained from microalgae. Besides lipids, carbohydrates are also valuable raw materials of microalgae. Various studies indicate that microalgae proteins are of high value and are comparable to conventional plant proteins. The simple cellular structure of microalgae also allows relatively simple genetic manipulation compared to, for example, plants.

The most important criteria influencing the quality of the microalgae biomass produced are the selection of the microalgae, the selection of the appropriate bioreactor system, the selection of the optimal conditions for microalgae cultivation, and the selection of the method for removing the desired microbial product. The conditions of microalgae cultivation in a bioreactor and the chosen bioreactor system therefore have a major influence on the production of the microalgae.

Biotechnological microalgae production is effected in open or closed bioreactor systems. Natural watercourses, lakes and lagoons, and also artificially excavated canals and basins, are usually used as open systems.

There are various constructive solutions for the closed bioreactor systems relating to the subject matter of the present invention, for example bioreactors in the form of pipes or plates in which the constantly liquid nutrient medium (often also referred to as growth medium or nutrient solution) in which the microalgae form is moved by use of pumps.

These bioreactors, by means of which microorganisms, such as microalgae for example, can be produced, i.e., cultivated and propagated, are commonly also referred to as photobioreactors, since they use carbon dioxide ($CO_2$) and light in a known manner for photosynthesis for the growth and propagation of the microorganisms.

EP 3 041 924 B2 already discloses a closed photobioreactor for obtaining phytoplankton, in which a housing contains a nutrient solution and a plurality of vertically oriented and horizontally spaced plates which are not to extend as far as the opposite wall and of which at least a portion is fixed to the top of the housing in order to form a vertically meandering flow. The plates are alternately fixed either to the bottom or to the top of the housing, with attachment of lighting means to the end faces of the plates that are situated in the region of fixation. The plates themselves consist of a transparent solid material, embedded in which are light-scattering particles of such a particle density that the density of the light emission across the surface of the plate is approximately constant. However, such a large-scale production system is altogether relatively complex in structure and hence expensive to manufacture.

Furthermore, EP 2 326 706 B1 discloses a closed photobioreactor for growth and reproduction of microorganisms that comprises a basin system containing a nutrient suspension, wherein the basin system comprises a vertically meandering system formed by partition walls, which are at least sectionally light-transmissive, in order to achieve a substantially vertical flow of the nutrient suspension in the basin system. In a technically extremely complicated manner, the partition walls here are hollow and filled with a dispersive liquid to divert light into the nutrient suspension.

SUMMARY OF THE INVENTION

In contrast, it is an object of the present invention to provide a photobioreactor, especially for production of microorganisms, most preferably microalgae, which is of simple construction, which is moreover simple to maintain and with which a high yield is achievable in conjunction with a high-quality product. It is a further object of the present invention to provide a suitable reactor vessel for such a photobioreactor. And lastly, it is a further object of the invention to provide a suitable method for producing microorganisms, especially microalgae, using such a photobioreactor.

These objects are achieved by the features of the independent claims. Advantageous embodiments are the subject matter of the dependent claims which refer back thereto.

According to the claims, there is provided a photobioreactor, especially for the production of microorganisms, most preferably microalgae, wherein the photobioreactor is designed as a closed reactor comprising a plurality of upwardly open reactor vessels which are closed (preferably closed in a gas- and/or liquid-tight manner) by at least one or a one-piece or multi-piece, preferably removable, top wall of the photobioreactor and in which a nutrient medium is accommodable. The basic function of the top wall is that of a lid to reduce contamination of the nutrient medium, or of the microorganisms produced, with impurities (e.g., solid particles from the air, bacteria, spores, etc.), and this leads to a high quality of the microorganisms produced. The top wall can preferably be opened at any time in order to facilitate access to the nutrient medium or growth medium and facilitate access for cleaning the reactor vessels. A nutrient medium is understood here to mean any suitable liquid growth medium which has been inoculated with nutrients in order to initiate the production of the particular desired microorganisms. In the case of microalgae, this can, for example, be osmosis water that has been inoculated with nutrients.

According to the invention, at least some of the reactor vessels, preferably all the reactor vessels, of the photobioreactor are designed as an individual vessel which, viewed in cross section, has in each case a U-shape with a front wall extending in the vertical axis direction and a back wall spaced apart therefrom in the longitudinal direction and likewise extending in the vertical axis direction that are connected to one another at the bottom by a bottom wall. The reactor vessels of the photobioreactor that are designed as an individual vessel as described above are arranged one after another as seen in the longitudinal direction of the photobioreactor (or flow-through direction of the nutrient medium), specifically in such a way that a front reactor vessel, as seen in the longitudinal direction, having an at least regionally light-transmissive back wall is adjacent to an at least regionally light-transmissive front wall of a rear reactor vessel, as seen in the longitudinal direction, with formation of gap or gap space, wherein the free end regions of the front and back walls adjacent to one another with formation of the gap have a common flow-over wall region which closes the gap from above, based on the vertical axis direction, and which has at least one vessel flow-over opening between the adjacent reactor vessels. Via said vessel flow-over opening, the nutrient medium can then flow over from a front reactor vessel, as seen in the flow direction, into a rear reactor vessel opposite it. The front wall and the back wall of the reactor vessel or the reactor vessels are preferably rectangular and/or plate-shaped.

The flow-over wall region, which can also be referred to as a flow-over wall region element, extends up to the top wall and is adjacent thereto. This adjacency is preferably effected in such a way that the flow-over wall region is adjacent to the top wall in a gas- and/or liquid-tight manner and/or is optionally even connected (preferably detachably connected) thereto.

In the gap between mutually adjacent reactor vessels (and hence below the flow-over wall region as seen in the vertical axis direction), there is accommodated at least one lighting element, by means of which light is emittable through the respectively assigned, at least regionally light-transmissive front wall and/or back wall into one of the two adjacent reactor vessels or into both adjacent reactor vessels.

Furthermore, in each of the reactor vessels designed as an individual vessel, there is provided a partition wall which is preferably connected to the bottom wall and/or rectangular and/or plate-shaped and which, proceeding from the bottom wall, extends upward in the vertical axis direction to the top wall and is adjacent thereto, preferably adjacent thereto in a gas- and/or liquid-tight manner and/or optionally even connected (preferably detachably connected) thereto, so that the partition wall divides the reactor vessel into a front reactor chamber and a rear reactor chamber, based on the longitudinal direction or flow direction.

Furthermore, in the partition wall, in the near-bottom-wall region of the partition wall that is adjacent and/or connected to the bottom wall, there is provided at least one partition-wall flow-through opening between the front and the rear reactor chamber.

With such a structure, a nutrient medium accommodated in the front reactor chamber of a front reactor vessel can flow through the at least one partition-wall flow-through opening into the rear reactor chamber of the front reactor vessel and then further flow upward and through the at least one vessel flow-over opening from the rear reactor chamber of the front reactor vessel into a front reactor chamber of a rear reactor vessel (vertically meandering flow).

The particular advantage of the solution according to the invention is that a plurality of essentially individual reactor vessels preferably designed as identical parts can be provided here, which reactor vessels can be manufactured in a simple manner, for example could even be manufactured by 3D printing. The individual reactor vessels can be joined together in basically any number and sequence in order to form a desired photobioreactor, the joining in this case being effected in such a way that the light-emitting lighting elements required for photosynthesis can be simultaneously arranged in a simple and functionally reliable manner in a gap or space between the respective back wall and front wall of mutually adjacent reactor vessels, in an advantageous dual role. The gap or space between the mutually adjacent reactor vessels is, at the same time, quickly accessible in a simple manner, especially also in connection with maintenance work and assembly work, meaning that lighting elements containing their lighting bodies can be exchanged and replaced in a simple manner. A technically complicated solution according to the prior art, in which lighting elements are to be arranged on the end face of plates, in which moreover light-scattering particles in a certain particle density are to be embedded in a particularly complicated manner, can therefore be completely dispensed with by the solution according to the invention, as can the provision of dispersive liquids in hollow partition walls that is likewise already known from the prior art. In the case of the solution according to the invention, the lighting means merely have to be arranged at the desired height in the externally accessible gap between the front and back walls of mutually adjacent reactor vessels.

Furthermore, said solution also has the advantage, compared to the solutions of the prior art, that the illumination or lighting of the reactor vessels or the reactor chambers can be individually adapted and changed in a simple manner. To this end, it is sufficient, for example, to modify the arrangement and orientation of the lighting elements, which can be done in a simple manner from outside the reactor vessel merely by engagement in the gap between the mutually adjacent reactor vessels. Moreover, the respective lighting conditions in the interior of the reactor vessels can be specified in a simple manner, for example such that regions differing in brightness, as seen in the flow direction, are formed, which is advantageous for the growth of microorganisms, especially microalgae, and will be more particularly elucidated below.

Moreover, the solution according to the invention with the singularized reactor vessels also has the advantage that, in the event of any damage to an individual reactor vessel or individual parts of a reactor vessel, it is only said individual reactor vessel that has to be exchanged.

And moreover, what thereby arises is a particularly advantageous modular system which can be supplemented or reduced by one or more reactor vessels in a particularly simple manner if this should be necessary in practical operation of the photobioreactor.

A particularly advantageous connection between the mutually adjacent reactor vessels is represented by the common flow-over wall region which closes the gap from above and which, as will be more particularly elucidated below, can, for example, be integral with one or possibly even both of the mutually adjacent reactor vessels or else, alternatively, can also be formed by a separate component.

At this point, it should be expressly clarified again that, according to the present concept of the invention, it is preferred that all the reactor vessels of the photobioreactor are designed as an individual vessel, as has been described above and will also be further described below. However, the scope of protection also expressly encompasses those embodiments of a photobioreactor in which only a portion, i.e., for example at least two, of the reactor vessels of the photobioreactor are designed as such individual vessels and the rest of the reactor vessels are constructed differently. Although the advantages of the invention then arise only for the individual vessels designed according to the invention and arranged one after another, said advantages are present nevertheless, and so such embodiments are also expressly encompassed by the scope of protection of the solution according to the invention. This must always be fundamentally noted in all of the following embodiments and developments, even if this is no longer expressly repeated.

According to a particularly preferred specific embodiment, the bottom wall, which is preferably arched, the partition wall, the front wall, the back wall and the flow-over wall region of at least one or at least some of the reactor vessels, preferably of all the reactor vessels, extend between two side walls, which side walls are opposite in the transverse direction and are preferably rectangular and/or plate-shaped, and are adjacent thereto, especially adjacent thereto in a gas- and/or liquid-tight manner and/or optionally even connected (preferably detachably connected) thereto. The side walls each extend up to the top wall and are adjacent thereto in order to provide the altogether closed structure of the reactor vessels. The adjacency of the side walls to the top wall is effected especially in a gas- and/or liquid-tight manner. Alternatively or additionally, the side walls can optionally even be connected to the top wall.

Particular preference is given to an embodiment in which the bottom wall of the reactor vessel is arched, wherein the vertex of the curvature is situated at the lowest point of the reactor vessel as seen in the vertical axis direction. Such an arched bottom wall region yields a particularly advantageous geometry which follows the flow path and which does not have any dead zones in which material, for example algae material, can accumulate in an undesirable manner. Moreover, it is particularly advantageous in this connection when the opposite side walls, which are preferably rectangular and/or plate-shaped, extend downward in the vertical axis direction at least as far as the vertex of the bottom wall and form a ground contact area. Altogether stably standing reactor vessels are then thereby provided despite the arched bottom wall region.

Particularly preferred in connection with a singularized design of the reactor vessels is a structure in which each individual reactor vessel designed as an individual vessel has two separate opposite side walls. This is because, as already described above, a separate component that is particularly easy to handle is formed as a result. In principle and as an alternative to this, however, there is of course also the possibility that two opposite large-area side walls form the side walls for a plurality of reactor vessels or all the reactor vessels. This does not conflict with the concept of individual vessels, which are then formed by the front wall, the partition wall and the back wall in this embodiment.

In order to enable light to enter the interior of the reactor vessels, it is necessary that, as described above, the front wall and/or the back wall of the reactor vessels that is/are assigned to lighting elements is/are light-transmissive at least in this assignment region. However, what is particularly advantageous and simple to manufacture is a structure in which at least one of the reactor vessels or at least some of the reactor vessels and/or the top wall is/are altogether light-transmissive and is/are preferably composed of a light-transmissive glass material or plastics material. Further preference is given to a structure in which the manufacture of the individual walls is with uniform material and/or as one piece and hence cost-effective.

As already stated above, it is moreover particularly advantageous when the front wall and/or the back wall and/or the partition wall and/or the flow-over wall region and/or the side walls are rectangular and/or plate-shaped. Such rectangular and/or plate-shaped wall elements can be manufactured in a simple manner and allow an altogether simple construction of the reactor vessel, especially with respect to the formation of identical parts.

The one-piece or multi-piece flow-over wall region can, for example, be integral with the front wall and/or the back wall of a reactor vessel, especially with the free end regions thereof. According to a first embodiment in relation to this, the flow-over wall region can, for example, be integral with either the front wall or the back wall of a reactor vessel, especially with the free end regions thereof. To form the common flow-over wall region, a free end region of a back wall or front wall of a directly adjacent reactor vessel is then likewise connected to the flow-over wall region. In this embodiment, the flow-over wall region then forms an integral part of a single reactor vessel and the assigned wall region of the adjacent reactor vessel can then be connected to the flow-over wall region in a very simple manner. A reduction in the diversity of components is thereby achieved. Moreover, such integral composite solutions are manufacturable in a simple and inexpensive manner.

Integrality with both the front wall and the back wall is possible too, for example when the flow-over wall region is two-piece and comprises both a front-wall-side flow-over wall region element and a back-wall-side flow-over wall region element that can be connected to one another. However, as an alternative to this, the flow-over wall region could also be one piece in the case of integrality with both the front wall and the back wall, and the interface in the event that singularization of individual reactor regions should be desired at all could be provided elsewhere, i.e., not in the region of the flow-over wall region.

Integrality within the meaning of the two preceding paragraphs preferably means a material-uniform and/or one-piece connection between the flow-over wall region (or the individual elements thereof) with the front wall and/or back wall of mutually adjacent reactor vessels, meaning that said reactor vessels then form modules which can be installed in a simple manner as part of final assembly.

At this point, it should moreover be expressly mentioned that it is not absolutely necessary to assemble the photobioreactor according to the invention from a plurality of individual reactor vessels, even if this is a preferred embodiment. The photobioreactor according to the invention comprising its plurality of reactor vessels can of course also be altogether one-piece, for example manufactured as one piece and with uniform material using a 3D printing process. The individual reactor vessels then form an altogether cohesive construct.

According to a further alternative embodiment, the flow-over wall region can also be formed by a separate one-piece or multi-piece component which is fixedly connectable or connected to the front wall and/or to the back wall of the two mutually adjacent reactor vessels, especially to the free end regions thereof. This preferably concerns those embodiments in which the flow-over wall region is formed by a separate component or by multiple separate components that is/are connected to the front wall and/or the back wall of the respective reactor vessel or the respective reactor vessels as part of preassembly, meaning that these preassembled reactor vessels then form preassembly modules which are only installed as part of subsequent final assembly.

According to a particularly preferred embodiment, the flow-over wall region is formed by a peripherally encircling frame having a vessel flow-over opening surrounded by the frame. Such a peripheral encircling frame ensures that the flow-over wall region is particularly stable. According to an embodiment particularly preferred in relation to this, a lower frame subregion in the vertical axis direction forms a connection region for the free end region of the front wall and/or the back wall of the respectively assigned reactor vessels and/or an upper frame subregion in the vertical axis direction is adjacent to the top wall, especially adjacent thereto in a gas- and/or liquid-tight manner and/or optionally even connected (preferably detachably connected) thereto.

The flow-over wall region can moreover have at least one flow guide element protruding into the vessel flow-over opening and/or a plurality of vessel flow-over openings preferably lying next to one another in the transverse direction. The plurality of vessel flow-over openings can be identical in shape or differ in shape. According to a particularly preferred embodiment, at least one connecting web running between frame parts, preferably at least one connecting web running in the vertical axis direction and between frame parts opposite in the vertical axis direction, is provided, especially in a dual role as flow guide element, to form a plurality of vessel flow-over openings. Such an arrangement with at least one flow guide element and/or with a plurality of flow-over openings and/or with at least one connecting web leads to advantageous relatively small turbulences and eddies in the region of the flow-over wall region, which has a particularly advantageous effect on the flow guidance and distribution of the microorganisms produced in the nutrient medium, since this counteracts any sedimentation tendency or accumulation tendency that may otherwise be present.

In connection with such flow guide elements or connecting webs, different shapes of the vessel flow-over openings can of course also be formed, which can likewise specifically contribute to forming certain desired flow conditions in the flow-over wall region.

The at least one lighting element can be designed in different ways and, for example, comprise one or more lighting bodies, the beam angle(s) and hence light cone(s) of which in the fitted state of the at least one lighting element is/are either fixed or else adjustable. In connection with a lighting body, the beam angle and hence light cone of which in the fitted state is adjustable, the illumination or lighting of the respective reactor chambers of the reactor vessels can be adapted and/or changed in an advantageous manner. As shown by the statements made above, the term "lighting element" is to be expressly interpreted in general terms in the context of the invention and can be understood to mean all suitable lighting means, such as, for example, LEDs and/or OLEDs. However, they can just as well also be understood to mean incandescent lamps, halogen spotlights or fluorescent tubes. The lighting elements used according to the invention, for example LED lights, emit light with an optimal wavelength and intensity that is tailored to the growth of the particular microorganisms, and are preferably also distinguished by high energy efficiency.

Furthermore, it is particularly advantageous when the at least one lighting element is arranged in the gap between the mutually adjacent reactor vessels in such a way that, in the at least one reactor chamber of the adjacent reactor vessels that is illuminated by the at least one lighting element, regions illuminated with differing brightness, especially as defined bright/dark regions, are formable or are formed. It is particularly preferred when regions which are illuminated with differing brightness and lie one after another in the flow direction are formed, especially as defined bright/dark regions. This is based on the inventor's finding that, when growing and propagating microorganisms, especially microalgae, it is particularly advantageous not to provide permanent and uniform lighting as seen in the flow direction. Specifically, permanent and uniform lighting can lead to an excessively high light intensity and hence to photoinhibition, which results in a reduction in the growth rate of microalgae. Photoinhibition occurs when the intensity of the light exceeds an intensity that ensures a maximum growth rate. On the contrary, according to the inventor's finding, it is particularly advantageous for the growth of microorganisms, especially microalgae, when brighter regions alternate with darker (less brightly illuminated) regions. In other words, this means that the microorganisms or microalgae in the less brightly illuminated regions then find a kind of quiet zone which has an altogether positive effect on the growth and propagation of the microorganisms or microalgae.

What is advantageous especially for forming regions illuminated with differing brightness in such a manner, but also in general, is an arrangement in which a plurality of lighting elements are accommodated in the gap between the mutually adjacent reactor vessels such that they are spaced apart from one another in the vertical axis direction and/or in the transverse direction. Using such an arrangement spaced apart in the vertical axis direction and/or in the transverse direction, it is possible to achieve lighting and illumination of the individual different regions of the reactor chambers that is advantageous and is exactly tailored to the particular desired individual case. It is particularly preferred that a plurality of rows of lighting elements extending in the transverse direction are formed which are spaced apart from one another, specifically preferably evenly spaced apart from one another, in the vertical axis direction.

Furthermore, it is preferred that the rows of lighting elements extending in the transverse direction are formed by a plurality of lighting elements spaced apart from one another and/or by light strips.

According to a particularly preferred embodiment, the distance between the lighting elements, especially the rows of lighting elements, is between 10 and 40 cm, preferably between 15 and 30 cm, in the vertical axis direction.

As already stated above, what can be set and achieved in connection with the arrangement of lighting elements according to the invention are very different lighting conditions in the individual reactor vessels or in the reactor chambers thereof. For example, to this end, lighting elements or rows of lighting elements that are spaced apart and follow one another in the vertical axis direction can be arranged in such a way that a lighting element/row of lighting elements or a first part of the lighting elements/rows of lighting elements emits light through the back wall (alternatively front wall) of the front (alternatively rear) reactor vessel, whereas the next lighting element/row of lighting elements in the vertical axis direction or the next part of the lighting elements/rows of lighting elements in the vertical axis direction emits light through the front wall (alternatively back wall) of a rear (alternatively front) reactor vessel. Such an arrangement would of course, alternatively or additionally, also be possible based on the transverse direction.

Alternatively, the lighting elements or rows of lighting elements can, however, emit light both through the back wall of a front reactor vessel and through the front wall of a rear reactor vessel. Other arrangements in groups are also possible in principle.

The statements just made demonstrate that there is a multiplicity of different options for arranging the lighting element(s) in the gap between mutually adjacent reactor vessels in order to create lighting conditions tailored to the particular purposes and applications. With the arrangement according to the invention of the lighting elements in the gap between mutually adjacent reactor vessels, this is possible in a particularly simple and advantageous manner in contrast to the prior art.

Furthermore, lighting elements can additionally also be arranged on the top wall, for example on the underside of the top wall. Alternatively or additionally, lighting elements can, however, also be arranged on the outside and topside of the top wall, specifically in connection with the light-transmissive top walls preferably used.

Furthermore, a stiffening element can be provided in the gap between the mutually adjacent reactor vessels in the transition region from the front wall and/or back wall to the bottom wall, preferably a stiffening element which downwardly closes the gap, which stiffening element extends over a specified length in the transverse direction, especially completely extends in the transverse direction between opposite side walls, where it is adjacent. Such an additional stiffening element, which lies at a distance below the flow-over wall region, serves to stabilize the structure as a whole.

Furthermore, in the wall region near the bottom wall, the partition wall can have a peripherally encircling frame region having a partition-wall flow-through opening surrounded by the frame region. It is preferred that a lower frame subregion in the vertical axis direction is adjacent to the bottom wall, especially adjacent thereto in a gas- and/or liquid-tight manner and/or connected (preferably detachably connected) thereto.

Furthermore, the partition wall preferably has at least one flow guide element protruding into the partition-wall flow-through opening and/or a plurality of partition-wall flow-through openings preferably lying next to one another in the transverse direction. In this connection, what can be provided, for example, is that the plurality of partition-wall flow-through openings are identical in shape or differ in shape. Furthermore, according to a particularly preferred embodiment, at least one connecting web running between frame parts, preferably at least one connecting web running in the vertical axis direction and between frame parts opposite in the vertical axis direction, is provided, especially in a dual role as flow guide element, to form a plurality of partition-wall flow-through openings. As has already been elucidated above in connection with the vessel flow-over opening of the flow-over wall region, the same advantages arise here, i.e., such an arrangement with at least one flow guide element and/or with a plurality of flow-through openings and/or with at least one connecting web leads to advantageous relatively small turbulences and eddies in the region of the partition wall, which has a particularly advantageous effect on the flow guidance and distribution of the microorganisms produced in the nutrient medium, since this counteracts any sedimentation tendency or accumulation tendency that may otherwise be present.

In connection with such flow guide elements or connecting webs, different shapes of the partition-wall flow-through openings can of course also be formed, which can likewise specifically contribute to forming certain desired flow conditions there.

According to a further particularly preferred embodiment of the present concept of the invention, at least one of the reactor vessels or at least some of the reactor vessels, preferably all of the reactor vessels, has/have at least one feed nozzle, preferably a plurality of feed nozzles spaced apart in the transverse direction, by means of which a medium, especially $CO_2$ or $CO_2$-containing medium, is introducible into the reactor vessel from outside the reactor vessel. Particular preference is given to an embodiment in which the at least one feed nozzle, preferably a plurality of feed nozzles spaced apart in the transverse direction, is arranged in the near-bottom-wall region of the reactor vessel, specifically preferably arranged in the region of the rear reactor chamber on the bottom wall and/or on the back wall. Using such feed nozzles, by means of which a specified medium, especially $CO_2$ or a $CO_2$-containing medium, is introducible into the reactor vessel from outside the reactor vessel, photosynthesis can be supported in an advantageous manner. What is moreover advantageously achieved by the addition of nozzles in the near-bottom-wall region of the reactor vessel, and in this case preferably in the region of the rear reactor chamber on the bottom wall and/or on the back wall, is that no material can accumulate there.

Particularly preferably, the mouth opening of the at least one feed nozzle is oriented in the flow direction, so that, when the medium is injected, the flow of the nutrient medium is supported in the flow direction.

The photobioreactor is further preferably designed in such a way that an inlet for the nutrient medium is provided on the forwardmost reactor vessel in the longitudinal direction or flow-through direction, preferably in the top wall and/or in the front wall and/or in the side wall of the forwardmost reactor vessel in the longitudinal direction or flow-through direction, which inlet is preferably an inlet by means of which the nutrient medium is feedable to the front reactor chamber of the forwardmost reactor vessel.

Said inlet is preferably coupled to a conveying device, by means of which a portion of the nutrient medium, preferably a portion of the nutrient medium extracted from a rear region of the photobioreactor, most preferably a portion of the nutrient medium extracted from the rearmost reactor vessel in the longitudinal direction or flow-through direction, is feedable to the front reactor vessel. Here, the conveying device simultaneously serves as a circulating device for the liquid nutrient medium.

In general, the liquid nutrient medium in the photobioreactor is to be circulated by means of a conveying device of any kind whatsoever in such a manner that a vertically meandering flow through the individual reactor vessels is formed.

The conveying device can in principle also be formed by a conventional pump, which, however, has the disadvantage that the cell walls of the microorganisms grown may be damaged. It is for this reason that, in the solution according to the invention, the conveying device according to a particularly preferred embodiment is formed by an air-lift arrangement in which a working medium, preferably air, most preferably $CO_2$-enriched and/or filtered air, is introduced into a nutrient medium line guided toward the inlet, so that the working medium conveys the nutrient medium in the direction of the inlet, especially takes it along in the manner of a carrier medium and conveys it in the direction of the inlet. As shown by the statements made above, although the lift arrangement is referred to here as an "air"-lift arrangement, this does not mean any restriction to the preferably gaseous working medium used. Specifically, instead of air as the working medium, a different carrier medium can also be used, for example an inert gas, to name just one further example of a working medium.

Furthermore, according to a particularly preferred embodiment, an outlet for the nutrient medium is provided on the rearmost reactor vessel in the longitudinal direction or flow-through direction, preferably in the top wall and/or in the back wall and/or in the side wall of the rearmost reactor vessel in the longitudinal direction or flow-through direction. The outlet is preferably designed in such a way that it can discharge the nutrient medium from the rear reactor chamber of the rearmost reactor vessel. Here, the outlet is, for example, designed as a drain, especially as an overflow, and/or coupled to an extraction device, by means of which the nutrient medium is extractable from the rearmost reactor vessel in the longitudinal direction or flow-through direction, especially extractable depending on the density of the microorganisms produced in the photobioreactor, for example in the rearmost reactor vessel.

Further preferably, downstream of the outlet is a continuous belt filter, especially a self-cleaning continuous belt filter, in which a continuous filter cloth is circulated between a filtering section and a section in which the filtered product is removed from the filter cloth. Therefore, if the desired density of the microorganisms produced, especially the desired algae density, has been reached, the nutrient medium can be at least partially discharged from the photobioreactor via the outlet and the desired product can then be separated from the nutrient medium in a separate station. It is possible to obtain the product in a particular gentle manner using the continuous belt filter, which, unlike the centrifuges generally used for this purpose, does not destroy the cell walls of the microorganisms obtained.

It is evident that the photobioreactor is operated in a closed circulation with regard to the liquid nutrient medium, i.e., the nutrient medium preferably present at the end of the photobioreactor and provided with microorganisms or microalgae is fed back to the inlet and this process is repeated, until the desired density of the particular product is reached and renewed (partial) discharge can be effected. It is further evident that, owing to the consumption of the nutrient medium, refeeding of nutrient medium must of course be effected periodically.

According to a further particularly preferred embodiment, a heating and/or cooling element is arranged on the outside of at least one reactor vessel, preferably on the bottom wall and/or in the near-bottom-wall region of the front wall and/or the back wall and/or the side walls of at least one reactor vessel, by means of which heating and/or cooling element the nutrient medium accommodated in the reactor vessel is temperature-controllable.

Further preferably, the one-piece or multi-piece top wall is preferably plate-shaped, so that it, for example, is easily handleable in connection with lifting of same.

Furthermore, particular preference is given to an embodiment in which the top wall is provided with at least one ventilation device, preferably with at least one ventilation fan, by means of which a gas, especially oxygen-containing gas, accumulating between the top wall and the nutrient medium is extractable from the interior of the photobioreactor, especially from the reactor vessels, wherein it is preferred that a top-wall-side ventilation device is assigned to each reactor vessel. This makes it possible to liberate especially the oxygen that has been generated between the top wall and the nutrient medium. In this way, the partial pressure of oxygen above the nutrient medium is lowered, thereby decreasing the proportion of oxygen in the nutrient medium. This is advantageous because an excessively high concentration of oxygen in the nutrient medium would result in a lower productivity of, for example, the microalgae biomass. Moreover, providing a ventilation device has the advantage that condensation on the top wall is minimized, which reduces cleaning and maintenance costs.

Furthermore, particular preference is given to a structure in which, in conjunction with a photobioreactor comprising a plurality of reaction vessels, all the reactor vessels have an identical U-shaped basic structure with a front wall and a back wall of substantially identical height, both of which have a gap space in relation to the top wall and both of which are overtopped by the partition wall which extends up to the top wall, where it is adjacent. The gap space in relation to the top wall in the region of adjacency between two reactor vessels is bridged by the flow-over wall region, which extends up to the top wall and is adjacent thereto. Furthermore, the front wall of the forwardmost reactor vessel in the longitudinal direction or flow-through direction has a first wall-type and/or plate-type bridging element which extends up to the top wall, where it is adjacent. The back wall of the rearmost reactor vessel in the longitudinal direction or flow-through direction has a second wall-type and/or plate-type bridging element which extends up to the top wall, where it is adjacent. Furthermore, the first and second wall-type and/or plate-type bridging element as well as all present front walls, partition walls and back walls and also the at least one flow-over wall region extend in the transverse direction between the side walls, where they are adjacent, which side walls likewise extend up to the top wall, where they are adjacent, so that a closed reactor is formed in the case of a fitted top wall. In the case of such a structure, the reactor vessels are essentially designed as identical parts, meaning that production and manufacture is substantially simplified.

In the present invention, "adjacency" of components to other components (especially "adjacency" of walls, wall regions or elements to other walls, wall regions or elements) is preferably understood to mean that the components directly rest against one another and/or rest against one another without a gap space, i.e., the components are in direct contact with one another in the case of adjacency and, for example, one of the walls rests against the other wall in a contact connection and is hence adjacent thereto. According to a further particularly preferred embodiment, each individual contact connection of said contact connections can be gas- and/or liquid-tight. Wherever mention is also made, in conjunction with adjacency of two components, of a possible connection between the two components as an optional embodiment, said connection can preferably be designed as a detachable connection, for example as a form-fit and/or snap-in connection, to name just one example. Such a preferred abutment and contact connection of the individual components yields an altogether stable structure, since the individual walls or wall regions then, for example, extend up to the top wall and can be supported there. This applies equally to the photobioreactor according to the invention and to the reactor vessel according to the invention and the method according to the invention.

The reactor vessel according to the invention for a photobioreactor, especially for a photobioreactor as has been described above, is distinguished by the fact that the reactor vessel is designed as an upwardly open vessel which, viewed in cross section, has a U-shape with a preferably rectangular and/or plate-shaped front wall extending in the vertical axis direction and a preferably rectangular and/or plate-shaped back wall spaced apart therefrom in the longitudinal direction and likewise extending in the vertical axis direction that are connected to one another at the bottom by a bottom wall. Furthermore, in the reactor vessel, there is provided a partition wall which is preferably connected to the bottom wall and/or rectangular and/or plate-shaped and which extends upward in the vertical axis direction proceeding from the bottom wall, so that the partition wall divides the reactor vessel into a front reactor chamber and a rear reactor chamber, based on the longitudinal direction. In the partition wall, in the near-bottom-wall region of the partition wall that is adjacent and/or connected to the bottom wall, there is provided at least one partition-wall flow-through opening between the front and the rear reactor chamber. As has already been stated above in connection with the photobioreactor according to the invention, such a reactor vessel is distinguished by a very compact and simple design, it being possible for said reactor vessel as an individual vessel to be combined in a simple manner with other reactor vessels of the same design or else similar design in order to form a photobioreactor having a desired number of reactor vessels arranged one after another as a cascade.

As already stated above in connection with the photobioreactor, a one-piece or multi-piece flow-over wall region can be assigned to the reactor vessel, especially to the free end region of the front wall and/or the back wall of the reactor vessel, for example be integrally connected thereto or be connected thereto as a separate component, the flow-over wall region extending in the transverse direction over the width of the reactor vessel and having at least one vessel flow-over opening. With regard to the resulting advantages and to further relevant design variants, we refer to the statements made above.

Further advantageous is one embodiment of the reactor vessel having side walls which are opposite in the transverse direction, such that the bottom wall, which is preferably arched, the partition wall, the front wall, the back wall and the flow-over wall region of the reactor vessel extend between the two side walls opposite in the transverse direction and are adjacent thereto, especially adjacent there in a gas- and/or liquid-tight manner and/or connected thereto. Here too, the side walls are again preferably rectangular and/or plate-shaped.

According to a particularly preferred embodiment, the bottom wall of the reactor vessel is arched, wherein the vertex of the curvature is situated at the lowest point of the reactor vessel in the vertical axis direction. The opposite side walls, which are preferably rectangular and/or plate-shaped, extend downward, as seen in the vertical axis direction, at least as far as the vertex of the bottom wall and form a ground contact area. Here too, with regard to further embodiment and the resulting advantages, we refer to the statements made above about the photobioreactor.

What was last mentioned also applies to the further particularly preferred embodiment of the reactor vessel being altogether light-transmissive, preferably composed of a light-transmissive glass material or plastics material.

Furthermore, it is advantageous that at least one feed nozzle, preferably a plurality of feed nozzles spaced apart in the transverse direction, is provided on the reactor vessel, by means of which feed nozzle(s) a medium, especially CO2 or a CO2-containing medium, is introducible into the reactor vessel from outside the reactor vessel. Here, it is preferred that the at least one feed nozzle, preferably a plurality of feed nozzles spaced apart in the transverse direction, is arranged in the near-bottom-wall region of the reactor vessel, specifically preferably arranged in the region of the rear reactor chamber on the bottom wall and/or on the back wall. In relation to this too, with regard to further embodiments and/or the resulting advantages, we refer to the statements made above in connection with the photobioreactor.

Here again, according to a preferred embodiment, the reactor vessel upwardly open as such can be closed, preferably in a gas-tight and/or liquid-tight manner, by at least one top wall which is preferably plate-shaped and/or removable, in order to form a closed reactor vessel, especially in connection with a photobioreactor composed of a plurality of reactor vessels.

Moreover, the reaction vessel preferably has a U-shaped basic structure with a front wall and a back wall of substantially identical height, both of which have a gap space in relation to the top wall and both of which are overtopped by the partition wall which extends up to the top wall, where it is adjacent. The gap space is bridgeable by a flow-over wall region and/or by a wall-type and/or plate-type bridging element that extends up to the top wall and is adjacent thereto in the fitted state. Furthermore, the wall-type and/or plate-type bridging element and/or the flow-over wall region in the fitted state extend(s) in the transverse direction between the side walls and is/are adjacent thereto, which side walls likewise extend up to the top wall, where they are adjacent, so that a closed reactor vessel is formed in the case of a fitted top wall. The resulting advantages have likewise been acknowledged in detail above in connection with the photobioreactor. In this respect, we refer to the statements made there in order to avoid further repetition.

And lastly, there is proposed a method according to the invention for producing microorganisms, especially microalgae, by means of a photobioreactor, especially by means of a photobioreactor as described above, in which the photobioreactor is designed as a closed reactor comprising a plurality of upwardly open reactor vessels which are closed by a one-piece or multi-piece, preferably removable, top wall of the photobioreactor, preferably closed in a gas- and/or liquid-tight manner, and in which a nutrient medium is accommodated.

According to the invention, at least some of the reactor vessels are designed as an individual vessel which, viewed in cross section, has a U-shape with a front wall extending in the vertical axis direction and a back wall spaced apart therefrom in the longitudinal direction and likewise extending in the vertical axis direction that are connected to one another at the bottom by a bottom wall. The reactor vessels of the photobioreactor that are designed as an individual vessel in such a manner are arranged one after another as seen in the longitudinal direction of the photobioreactor (or flow-through direction of the nutrient medium), specifically in such a way that a front reactor vessel, as seen in the longitudinal direction, having an at least regionally light-transmissive back wall is adjacent to an at least regionally light-transmissive front wall of a rear reactor vessel, as seen in the longitudinal direction, with formation of gap or gap space, wherein the free end regions of the front and back walls adjacent to one another with formation of the gap have a common flow-over wall region which closes the gap from above, based on the vertical axis direction, and which has at least one vessel flow-over opening between the adjacent reactor vessels. Via said vessel flow-over opening, the nutrient medium can then flow over from a front reactor vessel, as seen in the flow direction, into a rear reactor vessel opposite it. The front wall and the back wall of the reactor vessel or the reactor vessels are preferably rectangular and/or plate-shaped.

The flow-over wall region, which can also be referred to as a flow-over wall region element, extends up to the top wall and is adjacent thereto. This adjacency is preferably effected in such a way that the flow-over wall region is adjacent to the top wall in a gas- and/or liquid-tight manner and/or is optionally even connected, preferably detachably connected, thereto.

In the gap between mutually adjacent reactor vessels (and hence below the flow-over wall region as seen in the vertical axis direction), there is accommodated at least one lighting element, by means of which light is emittable through the respectively assigned, at least regionally light-transmissive front wall and/or back wall into one of the two adjacent reactor vessels or into both adjacent reactor vessels.

Furthermore, in each of the reactor vessels designed as an individual vessel, there is provided a partition wall which is preferably connected to the bottom wall and/or rectangular and/or plate-shaped and which, proceeding from the bottom wall, extends upward in the vertical axis direction to the top wall and is adjacent thereto, preferably adjacent thereto in a gas- and/or liquid-tight manner and/or optionally even connected (preferably detachably connected) thereto, so that the partition wall divides the reactor vessel into a front reactor chamber and a rear reactor chamber, based on the longitudinal direction or flow direction.

Furthermore, in the partition wall, in the near-bottom-wall region of the partition wall that is adjacent and/or connected to the bottom wall, there is provided at least one partition-wall flow-through opening between the front and the rear reactor chamber.

With such a structure, a nutrient medium accommodated in the front reactor chamber of a front reactor vessel can flow through the at least one partition-wall flow-through opening into the rear reactor chamber of the front reactor vessel and then further flow upward and through the at least one vessel flow-over opening from the rear reactor chamber of the front reactor vessel into a front reactor chamber of a rear reactor vessel (vertically meandering flow), meaning that a nutrient medium accommodated in the front reactor chamber of a front reactor vessel flows through the at least one partition-wall flow-through opening into the rear reactor chamber of the front reactor vessel and further flows from the rear reactor chamber of the front reactor vessel through the at least one vessel flow-over opening into a front reactor chamber of a rear reactor vessel (vertical meandering flow).

The resulting advantages have already been acknowledged in detail above in connection with the photobioreactor, and so reference is made to the statements made there in order to avoid repetition.

The invention will be more particularly explained below merely by way of example with reference to a drawing.

BRIEF DESCRIPTION OF THE FIGURES

FIG. 1 shows a schematic front view of an exemplary photobioreactor according to the invention with a view of the forwardmost reactor vessel in the direction of the arrow Z in FIG. 2a, FIG. 2a shows a schematic longitudinal cross section along the line A-A of FIG. 1.

DETAILED DESCRIPTION OF THE INVENTION

Figure 2B:
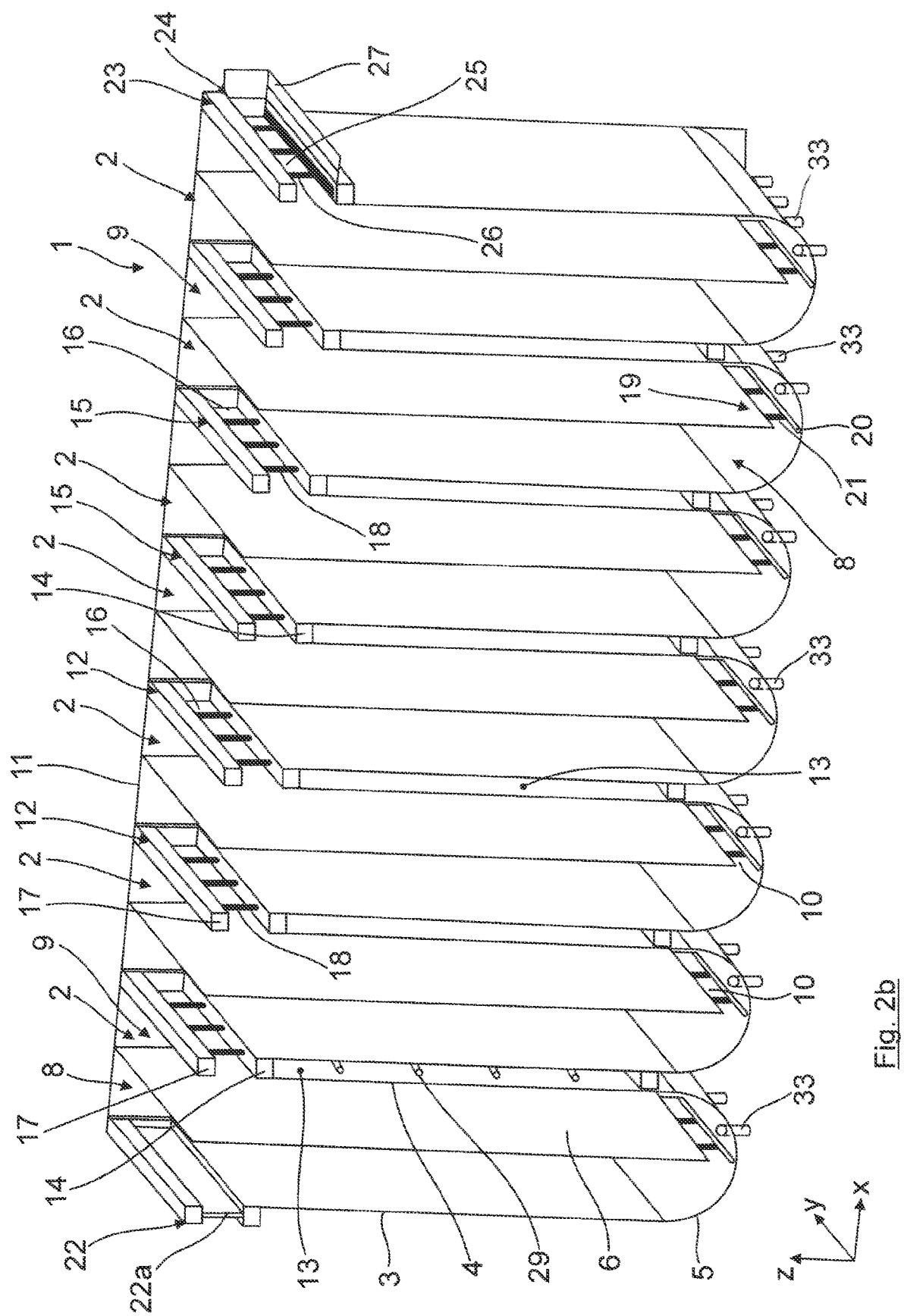
FIG. 2b shows a schematic perspective sectional view of the photobioreactor from FIG. 2a with features partially omitted.

Looked at together, FIGS. 1, 2a and 2b show an exemplary embodiment of a photobioreactor 1 according to the invention for production of microorganisms, especially production of microalgae. As is evident especially from FIGS. 2a and 2b, said photobioreactor 1 comprises a plurality of reactor vessels 2 which are designed as an individual vessel and in which a nutrient medium is accommodated.

As is evident especially from FIGS. 5, 6, 7 and 8 when looked at together, the individual reactor vessels 2 all preferably have an essentially identical U-shaped basic structure in which the reactor vessels 2 are each designed as an upwardly open vessel and have a front wall 3 extending in the vertical axis direction z and a back wall 4 spaced apart therefrom in the longitudinal direction x and likewise extending in the vertical axis direction z. The front wall 3 and the back wall 4 are both connected to one another at the bottom by a bottom wall 5.

Here, both the front wall 3 and the back wall 4 are plate-shaped and rectangular by way of example, whereas the bottom wall 5 is arched here by way of example.

Figure 6:
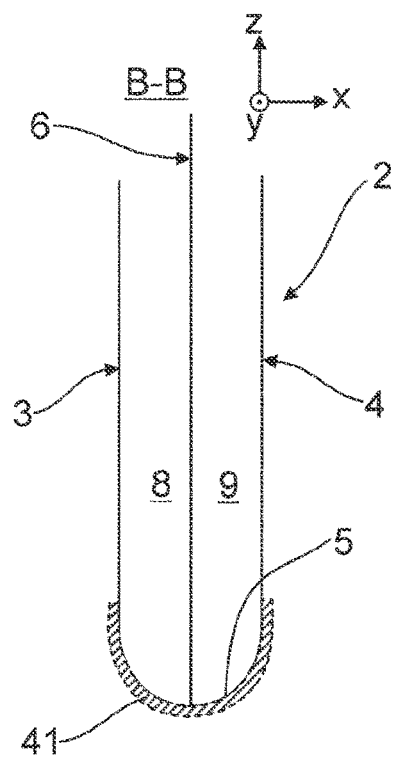
FIG. 6 shows a sectional view along the line B-B of FIG. 5.

As is evident especially from FIG. 6, the front wall 3 and the back wall 4 have a substantially identical height and are overtopped in the vertical axis direction z by a partition wall 6 arranged centrally in the reactor vessel 2 here by way of example. Said partition wall 6 is also plate-shaped and rectangular here by way of example, which is evident especially also from FIG. 8a, which shows an individual depiction of the partition wall 6.

In the fitted state (see, for example, FIG. 2a), the partition wall 6 extends upward in the vertical axis direction z, proceeding from the bottom wall 5, to a top wall 7, which is merely drawn in here with dashed lines for reasons of clarity and is, for example, likewise plate-shaped and rectangular. By means of its upper free end region in the vertical axis direction, the partition wall 6 is adjacent to the top wall 7, specifically preferably in a gas- and/or liquid-tight manner. Optionally, the partition wall 6 can also be connected to the top wall 7, specifically especially detachably connected thereto. The top wall 7 is depicted here as one piece, but may also be of multi-piece design.

As is evident especially from FIGS. 2a, 2b and 6, the partition wall 6 divides the reactor vessel into a front reactor chamber 8 and a rear reactor chamber 9, based on the longitudinal direction x.

Figure 8A:
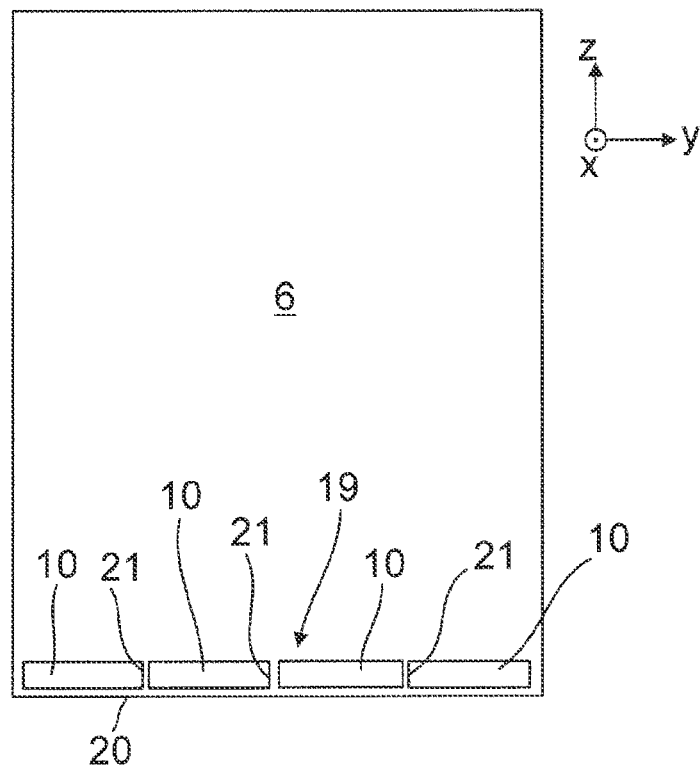
FIG. 8a shows an enlarged detailed view of a partition wall in a top view.

As is evident especially from FIG. 8a, what are formed in the partition wall 6, in the near-bottom-wall region of the partition wall that is adjacent and/or connected to the bottom wall 5, are a plurality of partition-wall flow-through openings 10 which enable the nutrient medium to flow over from the front reactor chamber 8 into the rear reactor chamber 9.

Figure 7:
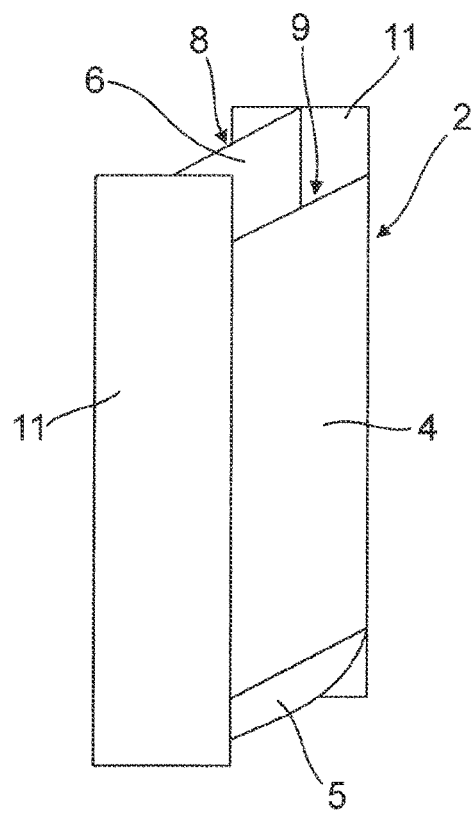
FIG. 7 shows a perspective view of the individual reactor vessel of FIGS. 5 and 6 with side walls.

The partition wall 6 as well as the front wall 3 and the back wall 4 extend, as seen in the transverse direction y, between two side walls 11 which are opposite in the transverse direction y and are likewise rectangular and plate-shaped here merely by way of example and which, as is evident especially from FIGS. 2a, 2b and 7, each extend up to the top wall 7 and are adjacent thereto, especially adjacent thereto in a gas- and/or liquid-tight manner and/or optionally even connected thereto. What was last mentioned also applies of course to the adjacency of the front wall 3, the partition wall 6 and the back wall 4 to the side walls 11.

At this point, it should be noted that the top wall 7 is preferably designed as a removable top wall, and so in this case either no connection may be provided or a detachable connection must be provided between the top wall 7 and the walls or wall regions adjacent thereto.

As is further evident from FIGS. 2a and 7 in particular, the vertex of the curvature of the bottom wall 5 of the reactor vessel is situated at the lowest point of the reactor vessel 2 as seen in the vertical axis direction z, and so the opposite side walls 11 extend downward, as seen in the vertical axis direction z, at least as far as the vertex of said bottom wall 5 and hence form a ground contact area.

In the exemplary embodiment of FIGS. 2a and 7 that is shown, each individual reactor vessel 2 has two separate opposite side walls 11. However, FIG. 2b depicts an alternative variant in which two opposite large-area side walls 11 both form the side walls for a plurality of reactor vessels 2 or, in the case of FIG. 2b, for all the reactor vessels 2.

Both the individual reactor vessels 2 and the top wall 7 are preferably altogether light-transmissive, for example composed of a light-transmissive glass material or plastics material.

As is further evident from FIG. 6 when looked at together with FIGS. 2a and 2b, all the reactor vessels 2 have an identical U-shaped basic structure with a front wall 3 and back wall 4 of identical height, both of which have a gap space in relation to the top wall 7 and both of which are overtopped by the partition wall 6 which extends up to the top wall 7.

In order to bridge the gap space in relation to the top wall 7, the photobioreactor 1 has, in the region of adjacency between two reactor vessels 2, a flow-over wall region 12 which will be described below and which extends up to the ceiling wall 7 as seen in the vertical axis direction z and between the opposite side walls 11 in the transverse direction y and is adjacent thereto in each case, especially adjacent thereto in a gas- and/or liquid-tight manner and/or optionally even connected thereto.

In the present case, said flow-over wall region 12 is, merely by way of example, formed by a separate component (see FIG. 3a) which is fixedly connected to the front wall 3 and the back wall 4 of two mutually adjacent reactor vessels 2 (see FIGS. 2a and 2b). As is further evident from FIGS. 2a and 2b, the individual reactor vessels 2 are arranged one after another in the longitudinal direction x in such a way that a front reactor vessel 2, as seen in the longitudinal direction x, having a light-transmissive back wall is adjacent to a light-transmissive front wall 3 of a rear reactor vessel 2, as seen in the longitudinal direction x, with formation of a gap 13 as assembly space. In the example shown here, the free end regions of the front and back walls 3, 4 assigned to the flow-over wall region 12 are each connected, especially connected in a gas- and/or liquid-tight manner, to a lower frame subregion 14 of a peripherally encircling frame 15 of the flow-over wall region 12. As a result, the mutually assigned front and back walls 3, 4 of the mutually adjacent reactor vessels 2 both have a common flow-over wall region 12 which closes the gap 13 from above, based on the vertical axis direction z, and has here, merely by way of example, a plurality of vessel flow-over openings 16.

Figures 3A, 3B:
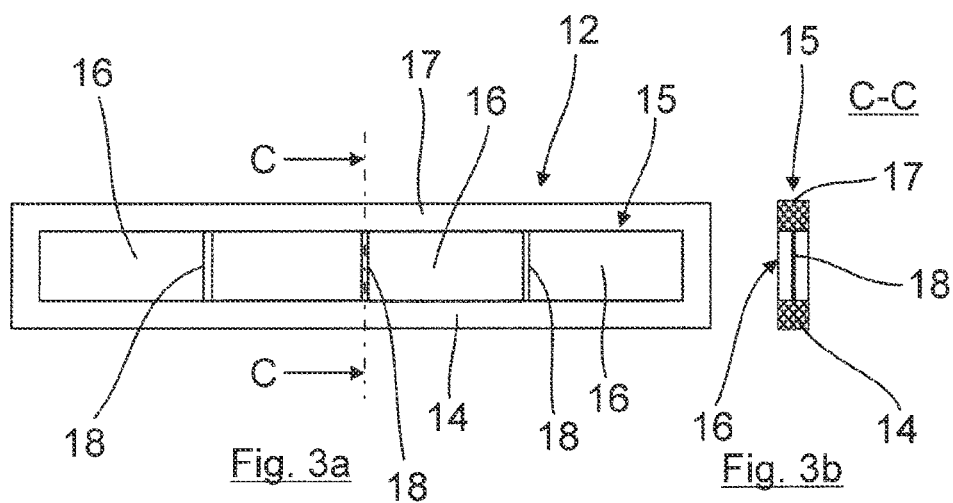
FIG. 3a shows a schematic exemplary embodiment of a flow-over wall region formed by a separate component.
FIG. 3b shows a schematic sectional view along the line C-C of FIG. 3a, FIG. 3c shows a schematic view of a further alternative embodiment of the flow-over wall region.

As is evident especially from FIG. 3a, the lower frame subregion 14 in the vertical axis direction z forms the connection region for the free end regions of the front walls 3 and back walls 4 of the assigned reactor vessels 2, whereas an upper frame subregion 17 in the vertical axis direction z is adjacent to the top wall 7, especially adjacent thereto in a gas- and/or liquid-tight manner and/or optionally even connected, preferably detachably connected, thereto.

The plurality of vessel flow-over openings 16 lying next to one another in the transverse direction are formed here by a plurality of connecting webs 18 which run in the vertical axis direction z between the upper frame subregion 17 and the lower frame subregion 14 and which preferably simultaneously form flow guide elements.

Figure 3C:
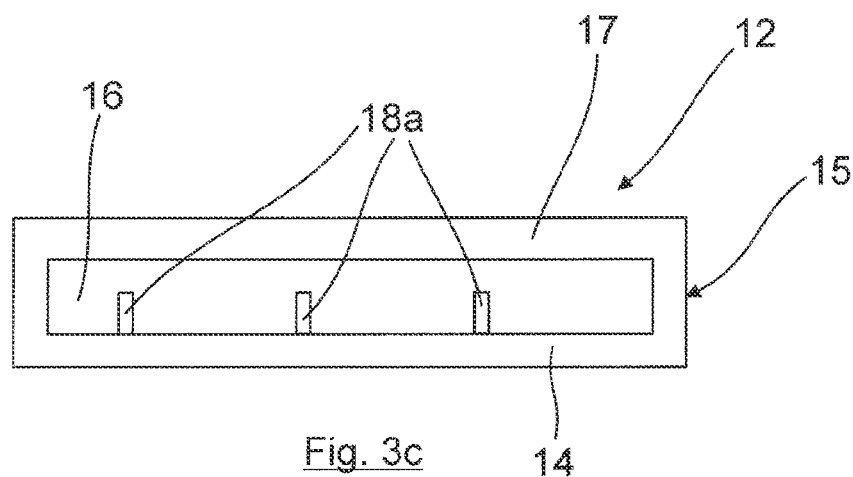

Alternatively, what could also be provided, however, is only a single vessel flow-over opening 16 without flow guide elements or connecting webs 18 (not depicted) or else a vessel flow-over opening 16 into which one or more flow guide elements 18a protrude, as is depicted in FIG. 3c merely by way of example.

As is evident especially from FIGS. 2a and 2b when looked at together, this arrangement of the flow-over wall region 12 between the mutually assigned front and back walls 3, 4 of mutually adjacent reactor vessels 2 gives rise to, in each case, an upper flow-over region, based on the vertical axis direction z, through which a nutrient medium can flow or flow over from a rear reactor chamber 9 of a front reactor vessel 2 into a front reactor chamber 8 of a rear reactor vessel 2.

According to an alternative embodiment, the flow-over wall region 12 can, however, also be integral with the free end region of the back wall 4 of the reactor vessel 2. This is shown schematically in FIG. 9a. Here, a free end region of a front wall 3 of a directly adjacent reactor vessel 2 is then likewise connected to the flow-over wall region 12 to form the common flow-over wall region 12 (see arrow 42).

According to a further alternative embodiment, the flow-over wall region 12 can, however, also be integral with the free end region of the front wall 3 of the reactor vessel 2. This is shown schematically in FIG. 9b. Here, a free end region of a back wall 4 of a directly adjacent reactor vessel 2 is then likewise connected to the flow-over wall region 12 to form the common flow-over wall region 12 (see arrow 42).

Figure 9A:
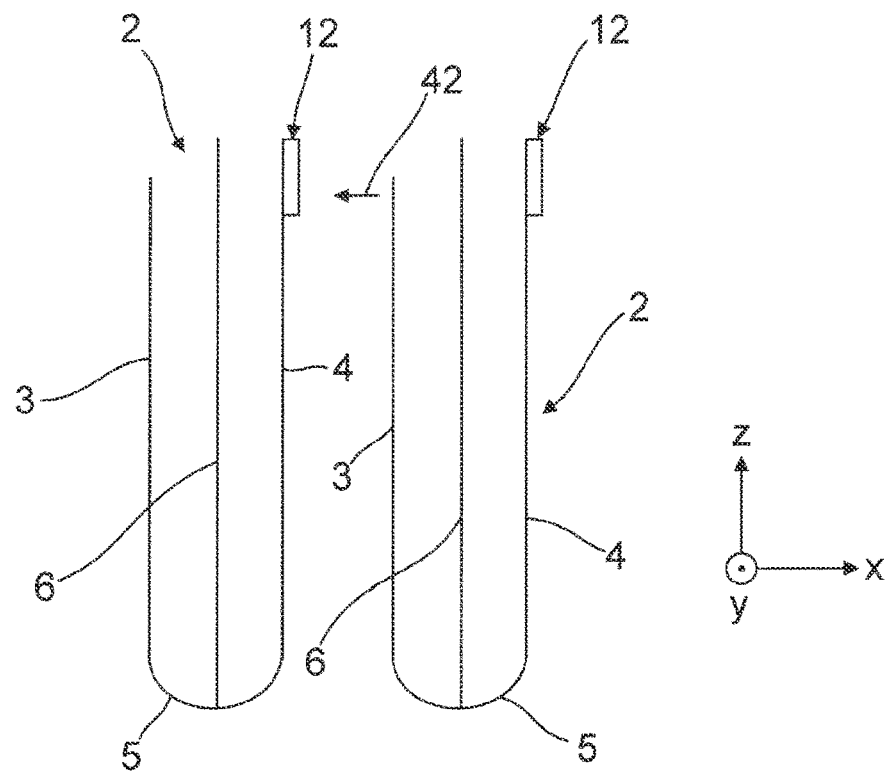
FIG. 9b shows a schematic view of an alternative embodiment of a flow-over wall region which is integral with the free end region of a front wall of a reactor vessel.
Figure 9B:
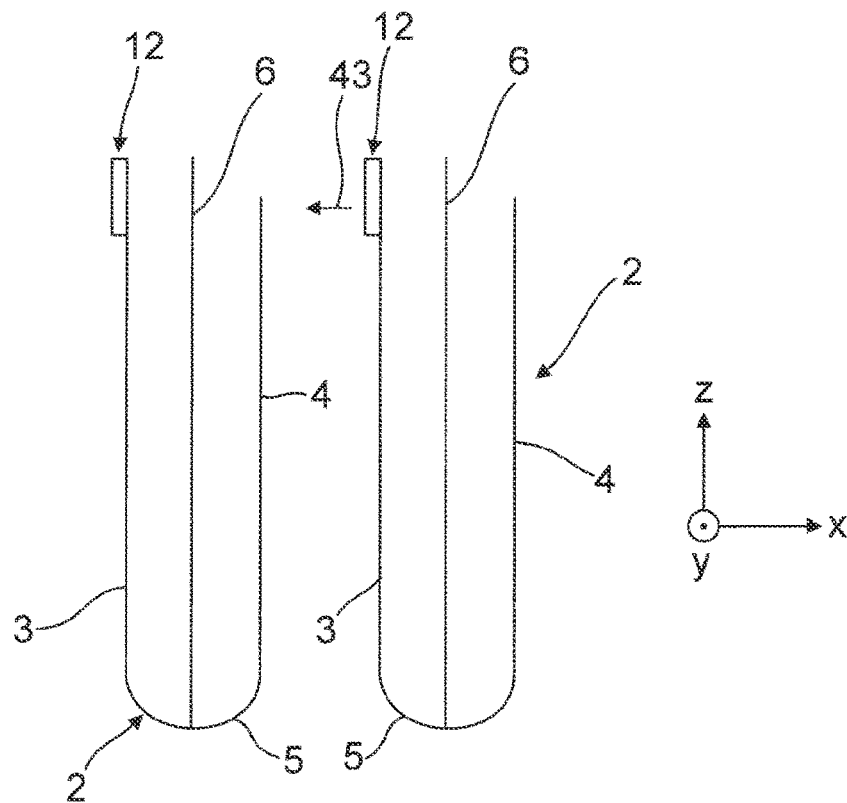

In an embodiment according to FIGS. 9a and 9b, it is evident that identical parts also arise in turn, since the reactor vessels 2 only have to be rotated 180° in order to form a flow-over wall region 12 arranged on a front wall 3 or a flow-over wall region 12 arranged on a back wall 4.

Figure 10:
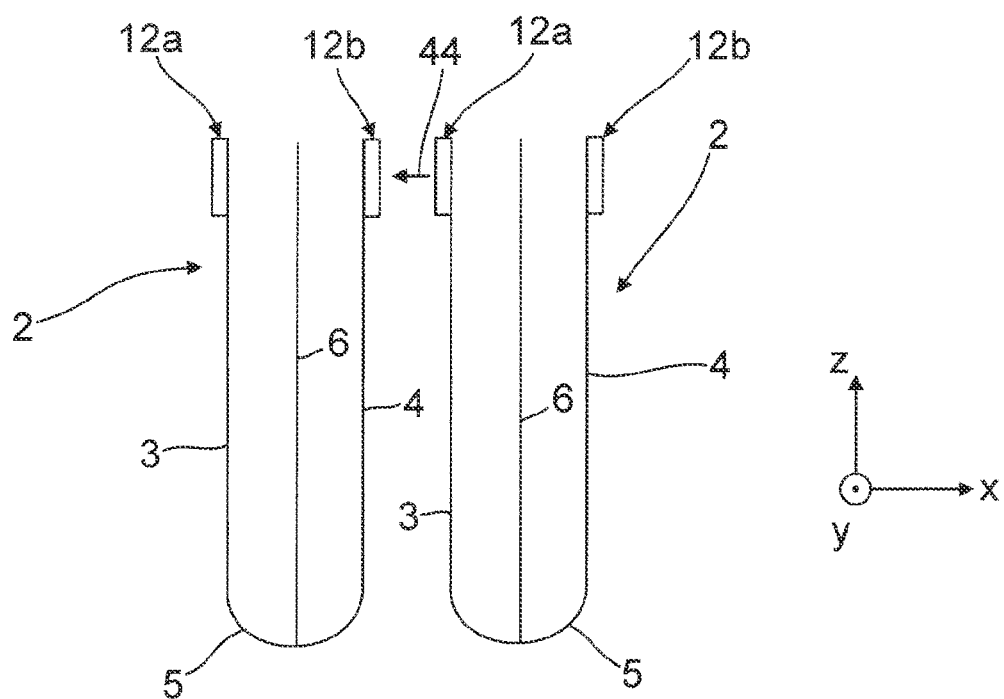
FIG. 10 shows a schematic view of a further alternative embodiment of a two-piece flow-over wall region, the flow-over wall region elements of which are integral with the free end region of the back wall and with the free end region of the front wall of a reactor vessel.

What was last mentioned also applies to the further alternative embodiment shown in FIG. 10, in which the flow-over wall region 12 is multi-piece and a first front-wall-side flow-over wall region element 12a is integral with the free end region of the front wall 3 of the reactor vessel 2 and a second back-wall-side flow-over wall region element 12b is integral with the free end region of the back wall 4 of the reactor vessel 2. The front-wall-side flow-over wall region element 12a and the back-wall-side flow-over wall region element 12b of two mutually adjacent reactor vessels 2 are then connected to one another to form the common flow-over wall region 12, which is indicated by the arrow 44 in what is depicted by FIG. 10. In principle, such a solution would also be possible with flow-over wall region elements 12a, 12b which are designed as separate components and only have to be connected to the free end regions of the assigned walls as part of preassembly.

A similar structure to the flow-over wall region 12 is also shown by the partition wall 6 in connection with its partition-wall flow-through openings 10, which have already been briefly addressed above.

As is evident especially from FIG. 8a, the partition wall 6 has, in the wall region near the bottom wall, a peripherally encircling frame region 19, whose lower frame subregion 20 in the vertical axis direction x is adjacent to the bottom wall 6, especially adjacent thereto in a gas- and/or liquid-tight manner and/or optionally even connected, preferably detachably connected, thereto.

Here, the partition wall 6 also has, by of example, a plurality of partition-wall flow-through openings 10 lying next to one another in the transverse direction y, which partition-wall flow-through openings are formed by a multiplicity of connecting webs 21 which run between opposite frame parts and which preferably simultaneously form flow guide elements.

As a result, the nutrient medium can also flow from the front reactor chamber 8 into the rear reactor chamber 9, and so an altogether vertically meandering flow path of the nutrient medium in the photobioreactor 1 arises.

Figure 8B:
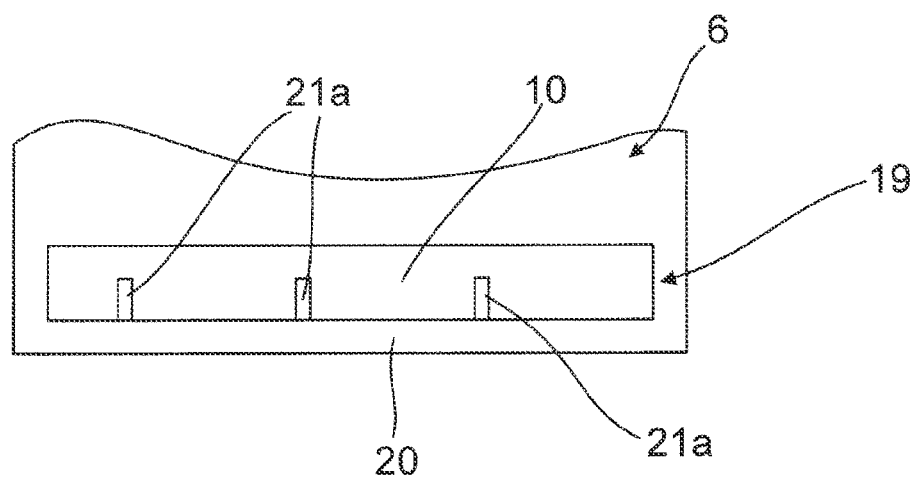
FIG. 8b shows an alternative embodiment of the partition-wall frame region of FIG. 8a, FIG. 9a shows a schematic view of an alternative embodiment of a flow-over wall region which is integral with the free end region of the back wall of a reactor vessel.

Alternatively, what could also be provided, however, is only a single partition-wall flow-through opening 10 without flow guide elements or connecting webs 21 (not depicted) or else a partition-wall flow-through opening 10 into which one or more flow guide elements 21a protrude, as is depicted in FIG. 8b merely by way of example.

As is further evident especially from FIGS. 2a and 2b, the front wall 3 of the forwardmost reactor vessel 2 in the longitudinal direction x or flow-through direction has a first wall-type and/or plate-type bridging element 22 which, proceeding from the free end region of the front wall 3, extends up to the top wall and is adjacent thereto, especially adjacent thereto in a gas- and/or liquid-tight manner and/or optionally even connected thereto.

The same applies in an analogous manner to the back wall 4 of the rearmost reactor vessel 2 in the longitudinal direction x or flow-through direction, which reactor vessel has a second wall-type and/or plate-type bridging element 23 which likewise extends up to the top wall 7 and is adjacent thereto, especially adjacent thereto in a gas- and/or liquid-tight manner and/or optionally even connected thereto.

Such a structure of a photobioreactor 1, in which bridging elements 22, 23 are used on the opposite free end sides of the photobioreactor 1 in addition to flow-over wall regions 12 in the region of adjacency between two reactor vessels 2, ensures that reactor vessels of an identical basic structure can be used in each case, specifically irrespective of the respective position of the reactor vessels in the photobioreactor.

The first and second bridging elements 22 and 23 are preferably separate components which have to be connected to the respective wall region of the reactor vessel 2. However, this is not a mandatory measure. In principle, it would namely also be possible for the front wall of the forwardmost reactor vessel 2 as well as the back wall of the rearmost reactor vessel 2 to be already formed from the outset with such a height that the front wall 3 of the forwardmost reactor vessel 2 as well as the back wall 4 of the rearmost reactor vessel 2 extend upward, in the vertical axis direction z, up to the top wall 7, where they are adjacent.

Figures 4A, 4B:
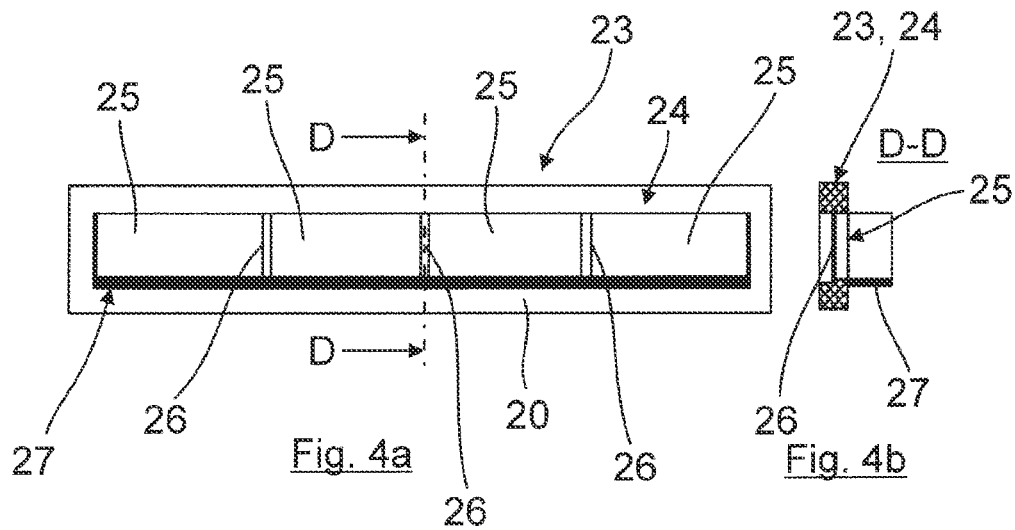
FIG. 4a shows a schematic detailed view of a bridging element forming an outlet.
FIG. 4b shows a section along the line D-D of FIG. 4a, FIG. 5 schematically shows a front view of an individual reactor vessel.
Figure 5:
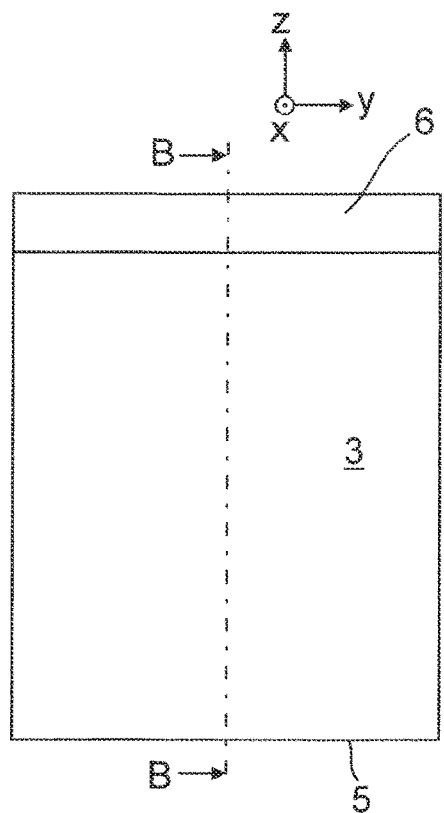

As is further evident especially from FIGS. 4a and 4b when looked at together, the second bridging element 23 can be designed essentially analogously to the flow-over wall region 12 of FIGS. 3a and 3b in order, for example, to form an outlet 24 having at least one outlet opening 25, preferably a plurality of outlet openings 25. Here too, the plurality of outlet openings 25 are again formed by providing connecting webs 26 between opposite frame subregions. Moreover, a nozzle-type overflow connection 27 extends outwardly from the mouth region of the outlet 24, so that a defined overflow is created, for example to a further photobioreactor connected thereto of essentially identical or same design or else as an outlet to a continuous belt filter 28 depicted here by way of example. Said continuous belt filter 28 will be described in more detail below.

Because the partition wall 6 and the flow-over wall region 12 and optionally also the bridging elements 22, 23 each extend up to the top wall 7 and are adjacent thereto, specifically preferably adjacent in a contact and abutment connection without a gap space, preferably adjacent in a gas- and/or liquid-tight manner, the result is an altogether stable structure, since the individual walls or wall regions then extend up to the top wall 7 and can be supported there, for example can also be accommodated in a groove-shaped recess, for example can also be detachably latched. What was last mentioned allows not only a particularly advantageous seal, but also a functionally reliable arrangement of the top wall 7 and of the individual walls and wall regions in the respectively desired position. For the partition wall 6, this additionally also applies in an analogous manner to the connection thereof to the bottom wall 5.

As is evident especially from FIG. 2a in conjunction with FIG. 2b, a plurality of lighting elements 29 are arranged in each case in the gap 13 between the mutually adjacent reactor vessels 2, specifically in such a way, by way of example here, that a plurality of rows of lighting elements 29a, 29b, 29c and 29d extending in the transverse direction y are provided which are spaced apart from one another in the vertical axis direction z, specifically preferably evenly spaced apart from one another in the vertical axis direction z as depicted here by way of example.

The individual rows of lighting elements 29a, 29b, 29c and 29d can, for example, be lighting elements 29 in the form of LED light strips, to name just one example, the LEDs of which as lighting bodies can emit light both through the front wall 3 and through the back wall 4 of two mutually adjacent reactor vessels into the respective reactor chambers of the reactor vessels 2. This is depicted merely by way of example in connection with the two reactor vessels 2 on the left in the image plane of FIG. 2a.

Alternatively, the lighting elements 29, for example in the form of LED light strips, can, however, also be arranged or formed in the gap 13 in such a way that light is alternately merely emitted into one of the two assigned reactor vessels 2, as depicted in connection with the two reactor containers 2 on the right in the image plane of FIG. 2a. In the example of the right-hand side of the image of FIG. 2a that is shown and not to be understood as definitive, the lighting elements 29 arranged above one another in the vertical axis direction z moreover, merely by way of example, alternately radiate here (as seen from top to bottom) through the back wall 4 of the front reactor vessel 2, then through the front wall 3 of the rearmost reactor vessel 2, then again through the back wall 4 of the front reactor vessel 2 and lastly again through the front wall 3 of the rearmost reactor vessel 2. It is evident that other arrangements and transilluminations are of course also always possible.

These two lighting situations, depicted merely by way of example in FIG. 2a, based on the lighting elements 29 or based on the rows of lighting elements 29a to 29d are intended to show that it is particularly advantageous to form regions illuminated with differing brightness 30, 31 in the respective reactor chambers 8, 9, said regions illuminated with differing brightness 30, 31 preferably being regions lying one after another in the flow direction of the vertical meandering flow. In the present example, the regions 30 are thus illuminated more brightly than the regions 31, thereby yielding a certain bright/dark effect which has an advantageous effect on the growth of microorganisms, in particular on the growth of phytoplankton such as microalgae.

In the solution according to the invention, flow-over through the partition wall 6 between the individual reactor chambers 8, 9 or flow-over through the flow-over wall region 12 between the individual reactor vessels 2 is then advantageously effected by flow-over openings 10, 16 which are tailored to the particular use and which can be geometrically designed in such a way that specific influencing of the flow conditions of the vertically meandering flow can be achieved in the particular flow-over region, for example in such a way that specific gentle turbulences or eddies can be brought about there, which, for example, counteract sedimentation movement of microorganisms produced, without impairing the flow path as such.

As is evident from FIGS. 2a and 2b, a stiffening element 32 can be provided in the gap 13 between the respectively mutually adjacent reactor vessels, preferably in the region above the transition region from the front and/or back wall 3, 4 to the bottom wall 5, for example a stiffening element 32 which downwardly closes the gap 13. Said stiffening element 32 can extend over a specified length in the transverse direction y, for example even completely extend between the opposite side walls 11.

As is moreover further evident from FIGS. 1, 2a and 2b when looked at together, a plurality of feed nozzles 33 spaced apart in the transverse direction are provided in each case in the near-bottom-wall region of the reactor vessels 2, here in each case in the region of the rear reactor chamber 9 on the bottom wall 5, by means of which feed nozzles a medium, especially CO2 or a CO2-containing medium, is introducible into the reactor vessel from outside the reactor vessel 2.

The mouth opening of the feed nozzles is preferably oriented in the flow direction (cf. especially FIG. 2a), so that, when the medium is injected, the flow of the nutrient medium is supported in the flow direction. Moreover, by means of such an injection, deposits in the rear reactor chamber, especially in the bottom wall region, may also be reliably avoided.

As is evident especially from FIGS. 1 and 2a when looked at together, the first bridging element 22 can be designed differently, for example as a closed wall element 22a (to the left of the dividing line T) or, analogously to the flow-over wall region 12, be provided with flow-over openings 22b (to the right of the dividing line T). This depends, for example, on how the photobioreactor 1 will be specifically used or employed. If the photobioreactor 1 will be used as an individual reactor or as the first reactor of a reactor cascade, then the first bridging element 22 can be designed as a closed wall element 22a and the nutrient medium is then run or fed in via the inlet 34, which is only drawn in schematically in FIG. 2a.

By contrast, if the photobioreactor 1 is part of a reactor cascade and does not form the first photobioreactor here, what can be provided is that the first bridging element 22 is provided with the flow-over openings 22b, which are then flow-coupled to the outlet 24 of a preceding photobioreactor 1, specifically preferably via the overflow connection 27 to which the first bridging element 22 is coupled (not depicted in detail here).

In connection with FIGS. 2a and 2b, the first bridging element 22 is designed here, by way of example, as a closed wall element 22a.

As is further evident from FIG. 2a, the inlet 34 is further coupleable to a feed line 34a, by means of which fresh nutrient medium 34a can be fed to the photobioreactor 1 at given times.

Furthermore, the inlet 34 is connected to a nutrient medium line designed here as a return line 34b, which, here by way of example, exits from the last reactor vessel 2 and by means of which the nutrient medium is circulated via the inlet 34. For this purpose, a pump as conveying device can in principle be switched into the return line 34b. However, the conveying device in the solution according to the invention is particularly preferably formed by an air-lift arrangement 35 in which a certain working medium, preferably air, most preferably CO2-enriched and/or filtered air, is introduced into the return line 34b guided toward the inlet 34, which working medium conveys the nutrient medium in the direction of the inlet 34.

As further depicted, in this circulation of the nutrient medium, a portion of the nutrient medium is preferably extracted from the rearmost reactor vessel 2 in the longitudinal direction x or flow-through direction and then fed back to the forwardmost reactor vessel 2 in the longitudinal direction x or flow-through direction. However, a deviation from this may also be made, for example in such a way that a plurality of return lines are provided which branch off from a plurality of reactor vessels and are guided toward the inlet. Alternatively or additionally, an inlet can equally also be provided in connection with other or further reactor vessels.

Here, the air-lift arrangement 35 thus simultaneously serves as a circulating device for the liquid nutrient medium in the photobioreactor 1, i.e., as a circulating device for guiding the nutrient medium in the desired manner through the photobioreactor 1 in a vertically meandering manner. As already frequently stated above, such an air-lift arrangement 35 is particularly gentle on the product. However, the invention can in principle can be carried out with any type of circulating device.

In the schematic embodiment in principle according to FIG. 2a, what is downstream of the photobioreactor 1 is the continuous belt filter 28, in which a continuous filter cloth 36 is circulated between a filtering section 37 and a section 38 in which the filtered product 39 is removed from the filter cloth 36. This is only depicted extremely schematically in FIG. 2a.

As can moreover be further gathered from FIG. 2a, the filtered nutrient medium 40 can optionally be returned to the nutrient medium circulation via a further return line 34c.

From FIG. 2a, it is moreover further evident that the feed nozzles 33 can likewise be coupled to a feed line 33a, via which, for example, CO2-enriched medium, for example CO2-enriched air, can be fed.

It is evident that valves, check valves and other blocking elements or control elements, by means of which media flow is controlled or regulated, can of course be arranged in the respective media-guiding lines in a customary manner.

Furthermore, a heating and/or cooling element 41 can be arranged on the bottom wall 5 of each of the reactor vessels, by means of which heating and/or cooling element the nutrient medium accommodated in the particular reactor container 2 can be appropriately temperature-controlled. This is only depicted by way of example and schematically in FIG. 6.

And lastly, the top wall 7 can be provided with one or more ventilation devices 45, which, for example, are formed by ventilation fans. This is only depicted extremely schematically and by way of example in FIG. 2a. By means of these ventilation devices 45, a gas, especially oxygen-containing gas, accumulating between the top wall 7 and the nutrient medium can be extracted from the interior of the photobioreactor 1, especially from the reactor vessels 2. In principle, a top-wall-side ventilation device 45 can be assigned to each reactor vessel 2.

LIST OF REFERENCE SIGNS

1 Photobioreactor
2 Reactor vessel
3 Front wall
4 Back wall
5 Bottom wall
6 Partition wall
7 Top wall
8 Front reactor chamber
9 Rear reactor chamber
10 Partition-wall flow-through openings
11 Side walls
12 Flow-over wall region
12a First flow-over wall region element
12b Second flow-over wall region element
13 Gap
14 Lower frame subregion
15 Frame
16 Vessel flow-over openings
17 Upper frame subregion
18 Connecting webs
18a Flow guide element
19 Frame region
20 Lower frame subregion
21 Connecting webs
21a Flow guide element
22 First bridging element
22a Closed wall element
22b Flow-over openings
23 Second bridging element
24 Outlet
25 Outlet openings
26 Connecting web
27 Overflow connection
28 Continuous belt filter
29 Lighting elements
29a Row of lighting elements
29b Row of lighting elements
29c Row of lighting elements
29d Row of lighting elements
30 More brightly illuminated region
31 More darkly illuminated region
32 Stiffening element
33 Feed nozzles
33a Feed line
34 Inlet
34a Feed line
34b Return line
34c Return line
35 Air-lift arrangement
36 Filter cloth
37 Filtering section
38 Section
39 Filtered product
40 Filtered nutrient medium
41 Heating and/or cooling element
42 Arrow
43 Arrow
44 Arrow
45 Ventilation device

The invention claimed is:

1. A photobioreactor being a closed reactor, the photobioreactor comprising:

a plurality of upwardly open reactor vessels configured for accommodating a nutrient medium;

a top wall of the photobioreactor being a one-piece or a multi-piece top wall for closing the reactor vessels;

at least some of said reactor vessels being formed as individual vessels which, in cross section, have a U-shape with a front wall extending in vertical axis direction, a back wall, spaced apart from said front wall in a longitudinal direction and also extending in the vertical axis direction, and a bottom wall connecting said front and back walls to one another at a bottom of the vessel;

said reactor vessels that are formed as individual vessels being arranged one after another in the longitudinal direction in such a way that a front reactor vessel has an at least regionally light-transmissive back wall adjacent to an at least regionally light-transmissive front wall of a rear reactor vessel, with a formation of a gap therebetween, wherein free end regions of said front and back walls adjacent one another have a common flow-over wall region which closes said gap from above, and which is formed with at least one vessel flow-over opening between said adjacent reactor vessels;

said flow-over wall region extending up to said top wall or to at least one piece of said multi-piece top wall and being adjacent thereto;

at least one lighting element disposed in said gap between mutually adjacent reactor vessels, said at least one lighting element being formed to emit light through a respectively assigned, at least regionally light-transmissive front wall and/or back wall into one of said mutually adjacent reactor vessels or into both said mutually adjacent reactor vessels;

a partition wall in each of said reactor vessels that are formed as individual vessels, said partition wall, proceeding from said bottom wall, extending upward in the vertical axis direction to said top wall and being adjacent thereto, with said partition wall dividing said reactor vessel into a front reactor chamber and a rear reactor chamber; and said partition wall, in a near-bottom-wall region of said partition wall that is adjacent and/or connected to said bottom wall, being formed with at least one partition-wall flow-through opening between said front and rear reactor chambers.

2. The photobioreactor according to claim 1, wherein:
said bottom wall, said partition wall, said front wall, said back wall, and said flow-over wall region of said reactor vessel extend between two side walls opposite in a transverse direction and are adjacent thereto; and
each of said side walls extends up to said top wall and are adjacent thereto.

3. The photobioreactor according to claim 2, wherein:
said bottom wall of said reactor vessel is arched, with a vertex of a curvature being situated at a lowest point of said reactor vessel in the vertical axis direction; and
opposite side walls extend downward, as seen in the vertical axis direction, at least as far as the vertex of said bottom wall and form a ground contact area.

4. The photobioreactor according to claim 2, wherein each of said individual reactor vessels has two separate opposite side walls.

5. The photobioreactor according to claim 1, wherein at least one of said reactor vessel or said top wall is altogether light-transmissive and composed of a light-transmissive glass material or plastics material.

6. The photobioreactor according to claim 1, wherein at least one of said front wall, said back wall, said partition wall, said flow-over wall region, or said side walls is rectangular and/or plate-shaped.

7. The photobioreactor according to claim 1, wherein said one-piece or multi-piece flow-over wall region is integrally formed with at least one of the free end region of said front wall or the free end region of said back wall of said reactor vessel.

8. The photobioreactor according to claim 7, wherein:
said flow-over wall region is integrally formed with the free end region of said front wall or with the free end region of said back wall of the reactor vessel and a free end region of said back wall or said front wall of a directly adjacent reactor vessel is also connected to said flow-over wall region to form a common flow-over wall region;
or
said flow-over wall region is a multi-piece wall region and a first front-wall-side flow-over wall region element is integrally formed with the free end region of said front wall of said reactor vessel and a second back-wall-side flow-over wall region element is integrally formed with the free end region of said back wall of said reactor vessel, wherein a front-wall-side flow-over wall region element and a back-wall-side flow-over wall region element are connectable to one another to form the common flow-over wall region.

9. The photobioreactor according to claim 1, wherein said flow-over wall region is a one-piece or multi-piece flow-over wall region formed by a separate component which is connectable to at least one of said front wall or said back wall of two mutually adjacent said reactor vessels.

10. The photobioreactor according to claim 1, wherein said flow-over wall region has a peripherally encircling frame and said vessel flow-over opening surrounded by said frame, with a lower frame subregion in the vertical axis direction forming a connection region for the free end region of said front wall and/or said back wall of the respectively assigned said reactor vessels and/or with an upper frame subregion in the vertical axis direction being adjacent said top wall.

11. The photobioreactor according to claim 1, wherein said flow-over wall region has at least one flow guide element protruding into said at least one vessel flow-over opening, and/or wherein a plurality of vessel flow-over openings are formed next to one another in the transverse direction.

12. The photobioreactor according to claim 11, further comprising at least one connecting web running between frame parts in the vertical axis direction and between frame parts opposite in the vertical axis direction, forming a flow guide element, to form a plurality of vessel flow-over openings.

13. The photobioreactor according to claim 1, wherein said at least one lighting element comprises one or more lighting bodies, and said lighting bodies have beam angles and light cones which, in a fitted state of said at least one lighting element are fixed or adjustable.

14. The photobioreactor according to claim 1, wherein said at least one lighting element is arranged in said gap between said mutually adjacent reactor vessels in such a way that, in said at least one reactor chamber of said mutually adjacent reactor vessels that is illuminated by said at least one lighting element, regions are illuminated with differing brightness when said at least one lighting element is energized.

15. The photobioreactor according to claim 1, wherein said at least one lighting element is one of a plurality of lighting elements accommodated in said gap between said mutually adjacent reactor vessels and spaced apart from one another in the vertical axis direction and/or in the transverse direction, and wherein a plurality of rows of lighting elements extending in the transverse direction are disposed with a spacing distance from one another.

16. The photobioreactor according to claim 15, wherein said lighting elements are evenly spaced apart from one another in the vertical axis direction and said rows of lighting elements extend in the transverse direction and are formed by a plurality of lighting elements spaced apart from one another and/or by light strips.

17. The photobioreactor according to claim 1, further comprising a stiffening element disposed in said gap between said mutually adjacent reactor vessels in a transition region from said front wall and/or said back wall to said bottom wall, said stiffening element extending over a specified length in the transverse direction between opposite side walls.

18. The photobioreactor according to claim 1, wherein said partition wall, in a wall region near said bottom wall, has a peripherally encircling frame region with a partition-wall flow-through opening surrounded by said frame region, and wherein a lower frame subregion in the vertical axis direction is adjacent to said bottom wall.

19. The photobioreactor according to claim 18, wherein said partition wall has at least one flow guide element protruding into said partition-wall flow-through opening and/or a plurality of partition-wall flow-through openings lying next to one another in the transverse direction.

20. The photobioreactor according to claim 18, further comprising at least one connecting web running between frame parts or at least one connecting web running in the vertical axis direction and between frame parts opposite in the vertical axis direction and forming a flow guide element defining a plurality of partition-wall flow-through openings.

21. The photobioreactor according to claim 1, wherein at least one of said reactor vessels is formed with at least one feed nozzle for introducing a medium into said reactor vessel from outside said reactor vessel.

22. The photobioreactor according to claim 21, wherein said at least one feed nozzle is arranged in a near-bottom-wall region of said reactor vessel, in a region of said rear reactor chamber on said bottom wall and/or on said back wall.

23. The photobioreactor according to claim 21, wherein a mouth opening of said at least one feed nozzle is oriented in a flow direction of the medium.

24. The photobioreactor according to claim 1, further comprising an inlet for a nutrient medium formed in a forwardmost reactor vessel in the longitudinal direction or flow-through direction, in at least one of a top wall, a front wall, or a side wall of the forwardmost reactor vessel.

25. The photobioreactor according to claim 24, wherein said inlet is coupled to a conveying device that functions as a conveying device and as a circulation device for the nutrient medium in the photobioreactor, by way of which a portion of the nutrient medium that is extracted from a rear region of the photobioreactor in the longitudinal direction or flow-through direction, is feedable to the forwardmost reactor vessel.

26. The photobioreactor according to claim 25, wherein said conveying device is formed by an air-lift arrangement in which a working medium, being air, CO2-enriched air, or filtered air, is introduced into a nutrient medium line guided toward said inlet, wherein the working medium conveys the nutrient medium in the direction of said inlet.

27. The photobioreactor according to claim 1, wherein an outlet for the nutrient medium is formed in a rearmost reactor vessel in the longitudinal direction or flow-through direction, in at least one of a top wall, a back wall, or a side wall of the rearmost reactor vessel, the outlet enabling a discharge of a nutrient medium from a rear reactor chamber of the rearmost reactor vessel.

28. The photobioreactor according to claim 27, wherein said outlet is a drain, an overflow drain, or is coupled to an extraction device, for extracting the nutrient medium from the rearmost reactor vessel in dependence on a density of the microorganisms produced in the photobioreactor.

29. The photobioreactor according to claim 28, further comprising a continuous belt filter disposed downstream of said outlet, wherein a continuous filter cloth is circulated in said continuous belt filter between a filtering section and a section in which filtered product is removed from the filter cloth.

30. The photobioreactor according to claim 1, further comprising at least one ventilation device in said top wall for extracting a gas that accumulates between said top wall and the nutrient medium from an interior of the photobioreactor, with a respective top-wall-side ventilation device being assigned to each reactor vessel.

31. The photobioreactor according to claim 1, wherein:
all of said reactor vessels have an identical U-shaped basic structure with a front wall and a back wall of substantially identical height, with said front wall and said back wall being disposed with a gap space relative to said top wall and being overtopped by said partition wall which extends up to said top wall and adjoins said top wall;
said gap space, in a region between two mutually adjacent reactor vessels, is bridged by said flow-over wall region, which extends up to said top wall and adjoins said top wall;
said front wall of a forwardmost reactor vessel in the longitudinal direction or flow-through direction has a first wall-shaped and/or plate-shaped bridging element which extends up to said top wall and adjoins said top wall;
said back wall of a rearmost reactor vessel in the longitudinal direction or flow-through direction has a second wall-shaped and/or plate-shaped bridging element which extends up to the top wall and adjoins said top wall; and
said first and second wall-shaped and/or plate-shaped bridging elements, all of said front walls, partition walls, and back walls, and said at least one flow-over wall region extend in the transverse direction between said side walls, and said side walls likewise extend up to said top wall, to thereby form a closed reactor when said top wall is mounted.

32. A method for producing microorganisms in a photobioreactor, the method comprising:
providing a closed reactor formed with a plurality of upwardly open reactor vessels which are closed by a one-piece or multi-piece top wall and in which a nutrient medium is to be accommodated;
wherein at least some of the reactor vessels are formed as individual vessels which, in cross section, have a U-shape with a front wall extending in a vertical axis direction, a back wall spaced apart therefrom in a longitudinal direction and likewise extending in the vertical axis direction, and a bottom wall connecting the front and back walls to one another;
wherein the reactor vessels of the photobioreactor that are designed as individual vessels are arranged one after another in the longitudinal direction in such a way that a front reactor vessel, as seen in the longitudinal direction, having an at least regionally translucent back wall is adjacent an at least regionally translucent front wall of a rear reactor vessel, as seen in the longitudinal direction, with formation of gap, wherein free end regions of the front and back walls adjacent to one another with formation of the gap have a common flow-over wall region which closes the gap from above and which has at least one vessel flow-over opening between the adjacent reactor vessels;
wherein the flow-over wall region extends up to and adjoins the top wall in a gas-tight and liquid-tight manner and/or is connected thereto;
accommodating at least one lighting element in the gap between mutually adjacent reactor vessels, and radiating light through the respectively assigned, at least regionally translucent front wall and/or back wall into one of the two adjacent reactor vessels or into the two adjacent reactor vessels;
wherein each of the reactor vessels of the photobioreactor that are designed as individual vessels contain a partition wall which proceeds from the bottom wall, extends upward in the vertical axis direction to the top wall to adjoin the top wall in a gas-tight and liquid-tight manner, wherein the partition wall divides the reactor vessel into a front reactor chamber and a rear reactor chamber along the longitudinal direction; and
providing in the partition wall, in a near-bottom-wall region of the partition wall that is adjacent and/or connected to the bottom wall, at least one partition-wall flow-through opening between the front reactor chamber and the rear reactor chamber, and enabling a nutrient medium accommodated in the front reactor chamber of a front reactor vessel to flow through the at least one partition-wall flow-through opening into the rear reactor chamber of the front reactor vessel and to further flow through the at least one vessel flow-over opening from the rear reactor chamber of the front reactor vessel into a front reactor chamber of a rear reactor vessel.

33. The method according to claim 32, which comprises providing the photobioreactor according to claim 1 and producing microalgae in the reactor vessels of the photobioreactor.

* * * * *